(12) United States Patent
Noti

(10) Patent No.: US 6,881,834 B1
(45) Date of Patent: Apr. 19, 2005

(54) MYELOID CELL PROMOTER AND CONSTRUCTS CONTAINING SAME

(75) Inventor: John D. Noti, Athens, PA (US)

(73) Assignee: Guthrie Foundation for Education and Research

( * ) Notice: Subject to any disclaimer, the term of this patent is extended or adjusted under 35 U.S.C. 154(b) by 0 days.

(21) Appl. No.: 09/476,202

(22) Filed: Jan. 3, 2000

(51) Int. Cl.⁷ .............................................. C07H 21/04
(52) U.S. Cl. ..................... 536/24.1; 536/23.1
(58) Field of Search .............................. 435/23.1, 24.1; 536/23.1, 24.1

(56) References Cited

U.S. PATENT DOCUMENTS

| | | |
|---|---|---|
| 5,502,176 A | 3/1996 | Tenen et al. |
| 5,556,954 A | 9/1996 | Burn et al. |

OTHER PUBLICATIONS

J. Noti et al., Human p150,95 α–Subunit: Genomic Organization and Analysis of the 5'–Flanking Region. *DNA and Cell Biol.*, vol. 11, pp. 123–138 (1992).

A. Back et al., Leukocyte Integrin CD11b Promoter Directs Expression in Lymphocytes and Granulocytes in Transgenic Mice. *Blood*, vol. 5, No. 4, pp. 1017–1024 (1995).

K. Ritchie et al., The Human Leukocyte Integrin CD11a Promoter Directs Expression in Leukocytes of Transgenic Mice. *Blood*, vol. 85, No. 1, pp. 147–155 (1995).

M. Van der Vieren et al., A Novel Leukointegrin, αdβ2, Binds Preferentially to ICAM–3. *Immunity*, vol. 3, pp. 683–690 (1995).

D. Wong et al., Cloning and Chromosomal Localization of a Novel Gene–Encoding a Human $β_2$–Integrin α Subunit. *Gene*, vol. 171, pp. 291–294 (1996).

T. Brocker et al., Targeted Expression of Major Histocompatibility Complex (MHC) Class II Molecules Demonstrates that Dendritic Cells Can Induce Negative but Not Positive Selection of Thymocytes In Vivo. *J. Exp. Med.*, vol. 185, No. 3, pp. 541–550 (1997).

C. S. Shelley et al., Mapping of the Human CD11c (ITGAX) and CD11d (ITGAD) Genes Demonstrates that they are Arranged in Tandem Separated by No More Than 11.5 kb. *Genomics*, vol. 49, pp. 334–336 (1998).

K. Garber, Waiting for Cancer Vaccines. *Mod. Drug Discovery*, pp. 37–44 (1999).

*Primary Examiner*—James Ketter
*Assistant Examiner*—Konstantina Katcheves
(74) *Attorney, Agent, or Firm*—Foley & Lardner LLP

(57) ABSTRACT

The present invention provides novel myeloid cell specific promoters, and cis-acting elements that influence the activity of a myeloid cell specific promoters, as well as promoter-heterologous gene constructs and transfected myeloid cells which include the novel promoters and/or the novel cis-acting elements. The present invention also provides a method of transfecting myeloid cells and a method of producing a selected product within the transfected cells. The invention also includes a method for identifying factors that can regulate myeloid cell specific transcription.

7 Claims, 26 Drawing Sheets

FIGURE 1a
(SEQ ID NO: 1 and SEQ ID NO: 2)

```
                                                                                      -1101
TTTAATCATG  GAATATTTCA  AACATACAGA  AAAATCACAG  AAAATAAATA  ACAACCACTC  ATTTATCTTC

-1031
TCCCCAACCC  CATGTAATAA  ATATTAAAAT  ATTGTGTTAA  ATGCTAAATT  TAACACATGC  TAAAGGTTCC

-961
TGGCTGGATG  TGGTGGCTCA  CGCCTGTAAT  CCCAGTACTT  TGGGAGGAGG  AGGTGGGAGG  ATTGCTTGAG

-891
TCCAGGAGCT  CGAGACCAGC  ATGGGCAACA  TAGTGCGATC  TCGTCTCTAC  AAAAAACAAA  AAAATTAGCT

-821
GGGCATGGTG  GTGTGCATCA  GTAATCCCAG  TGACTGGGAG  GCTGAGGTGG  GAGAATTGCT  TGAGTCTGGG

-751
AATTTGAGGC  TGCAGTGAGC  CCTGATCATG  CCACTGCATT  CCAGCATGGG  CGACATAGCA  AAACTTGTCA

-681
AAAAAAAAAA  AAGTTCCTC   TCTGCCCCAC  CATAGACAAC  CACTCTTCTG  ATTTCTATCT  TCGTAGATGA

AP1                                                -611
ATTTTGCCCA  TTCTCTTGTA  TATGAAAGGA  ACCAGACATT  AGGCATTCTG  GTGTCTGGTT  TCTTTCACTT
                                        ‾‾‾‾‾‾
                                                                                       -541
AAGATAAAAT  TGAGTTAACC  TGTATTGTTG  TACAGAACTG  CAGTTTGTTC  TTTGTTATTT  ATTGTAAAGA

-471
CAGGGTCTGG  CTATGTTGCC  TAGGCTGGTC  TCGAACTGTT  GGCCTCAAGC  AATCCACCTG  CCAAGCTCTG

-401
GGACCACAGG  CATGAGCCAT  GGCATCTGAT  CKGTAGTTTG  ATCTTATTTC  TTGCTGAGTA  GTAGCCCATG
    AP1                                                                                -331
GCATGACTTT  ATTATTTTGG  GTGTCCATTC  TCCTCTGGAG  GGGCTCTGCT  TTTTGAAACC  ACACCCTGGC
   ‾‾‾‾‾‾‾
            Ets                                                                        -261
CTAGCTCCCC  TTCTCCCTGC  CTCTCTGCAG  GCTCACATCC  ACATGCCAAG  ACCTCTGCAG  CCATTCTGCT
            ‾‾‾‾‾‾‾‾‾‾
    Ets                                                                                -191
TCCTGTCCTT  CCACTCCTGT  GGGACCTCAG  AGAGCTACGG  GGCTCCCTGG  GTACCAACTG  GCTCCTGAGG
‾‾‾‾‾‾‾‾‾‾                                                                                ‾‾‾‾
  Sp1/Sp3                                                             Sp1/Sp3          -121
CCTGGGGGAG  GGTGGTCTTC  TGGGAGAAGG  AAGCCAGGTC  CCTGCAGGTT  GTGGAGGGGG  ACAGAATGAG
‾‾‾‾‾‾‾‾‾‾                                                        ‾‾‾‾  ‾‾‾‾‾‾‾‾‾‾
                        Sp1/Sp3                                          Ets    -51
GGTTTTCCC   CAGGATGTTG  TTGGCCCCTG  CCCCCACTTC  TGTTCCATAA  TTAACCACGC  CCCTCCTACC
                   ‾‾‾  ‾‾‾‾‾‾‾‾‾‾  ‾‾‾‾‾‾‾‾‾                                ‾‾‾‾‾‾‾‾‾
                        Sp1/Sp3                 +1                              20
CACTGTGCCC  CTCTTCCTGC  TGTGTGGAGG  CCCTGAATCA  TTATTTTAAC  TACCCCCTGG  GAGGGTGAGC
                   ‾‾‾  ‾‾‾‾‾‾‾‾‾‾  ‾‾‾‾‾‾‾‾‾
   Ets                  Ets                                                       90
ACCTTCTGTG  CTCTGTCCCC  AACCTTCCAC  TTCCCCTCAA  CGCGCTGCTC  AGGG[ATG]ACC  TTCGGCACTG
    ‾‾‾‾‾‾              ‾‾‾‾‾‾‾‾‾‾                                   M  T    P  G  T
```

FIGURE 1a (continued)

```
                                                                                    160
TGCTTCTTCT  GAGTGgtaag  tggggccagg  gtgctgggga  gaagcttgga  ggagttctga  ggggactcca
 V  L L  L    S                                                                     230
tctgggaggg  caggctgggg  gctggtggtc  ggctccaacc  actcttatga  ggagctgagg  caggggagtg
                                                                                    300
cttcatgtgc  gagtggcccg  gagtcagtag  agtgtgacct  gaatgaagag  gggctcaggg  gctgtgctca
                                                                                    370
ggtggcgact  aagctacctc  tccagctggc  tatgttgtcc  caggcttccc  tgctcccact  catggagtcc
                                                                                    440
ctggtgtggg  tgacagaggt  ctccccagcc  tcccccggga  gtggaagcc   acagaagcca  ccagggaggg
                                                                                    510
ggaaaggttg  gacatcacct  ccctgggcct  nnnnnttccc  ccaagtcctg  actgcacgta  gggaagaggc
                        INTRON 1                                                    580
cccctgctga  aaactgcatc  agagtcacat  tcacgtgcca  tcaaaaatca  ggcttggctg  ggtgcggtgg
                                                                                    650
ctcatgctta  taatcccagc  actttgggag  gccgagatgg  gcgtatcccc  tgaggtcagg  agtttgtgac
                                                                                    720
cagcctggcc  aacatggtga  aaccccatct  ttaccaaaaa  tataaaaatt  agccgggcat  ggtggcgtgc
                                                                                    790
acttgtaatc  ccagctactt  gggaagctga  ggcaagagaa  tcgcttgaac  ccaggagacg  gaagttgcag
                                                                                    860
tgagctgaga  tcgtgccgtt  gcactccagc  ctcagcaaca  gagcgagact  ccatctcaaa  aaaaaaaaaa
                                                                                    930
aaaaaagaa   aaaaaagaaa  aagaggctgg  gaggtcctag  ggattggggc  ttctttaact  cccagcctcc
                                                                                   1000
ccgcccacca  aatattcctc  agTCCTGGCT  TCTTATCATG  GATTCAACCT  GGATGTGGAG  GAGCCTACGA
                         V  L  A     S  Y  H    G  F  N L   D  V  E    E  P  T
```

FIGURE 1b
(SEQ ID NO: 1 and SEQ ID NO: 2)

```
TCTTCCAGGA GGATGCAGGC GGCTTTGGGC AGAGCGTGGT GCAGTTCGGT GGATCTCGgt aggcccact        1070
 I F Q E   D A G       G F G       Q S V V     Q F G       G S R
                                   INTRON 2 (3019 bp)

ccccaagtg  cccgctgctc  ccacccctcc  tgtggctgca  gtgacatggc  catggttgtg  tctccagACT   4080
                                                                                 L
cgtggtgga  gcaccctgg   aggtggtggc  ggccaaccag  acgggacggc  tgtatgactg  cgcagctgcc   4150
 V V G     A P L       E V V A     A N Q       T G R       L Y D C     A A A
accggcatgt gccagccat   cccgctgcac  Agtgagtgac  cacctgggaa  ttgggcccct  caaccctcct   4220
 T G M     C Q P I     P L H
                       INTRON 3
ggaccccact gtgccccgc   ttagcttcca  gtccagaact  tccccgcaaa  tgagtgtgtg  ctgtgagtga   4290
gaccccgcgt gtctgccctt  gcagTCCGCC  CTGAGGCCGT  GAACATGTCC  TTGGGCCAGC  CCCTGGCAGC   4360
                       I R         P E A V     N M S       L G L       T L A A
CTCCACCAAC GGCTCCCGGC  TCCTGgtgag  tgagtgtctt  gggccacggg  ggggtggggt  ggggcggggg   4430
 S T N     G S R       L L
gtgttgttgg ggaggaggct  ggggctggga  gtgaaggagg  agggactcct  aggactcct   ggctcacagg    4500
                                   INTRON 4
cttctgcctc cagGCCCTGTG GCCCGACCCT GCACAGAGTC TGTGGGGAGA ACTCATACTC AAAGGGTTCC       4570
            A C         G P T L     H R V      C G E      N S Y S    K G S
TGCCTCCTGC TGGGCTCGCG  CTGGAGATC  ATCCAGACAG  TCCCCGACGC  CACGCCAGgt  aggtccctgg    4640
 C L L     L G S R     W E I       I Q T       V P D A     T P caggagctgc aggaggggt   tgggcccccg  cagtgcatct  ccgattcctc  cccattcccc  cacagAGTGT   8840
                                   INTRON 5 (4267 bp)                       E C
CCACATCAAG AGATGGACAT  CGTCTTCCTG  ATTGACGGCT  CTGGAAGCAT  TGACCAAAAT  GACTTTAACC   8910
 P H Q     E M D I     V F L       I D G       S G S I     D Q N       D F N
AGATGAAGGG CTTTGTCCAA  GCTGTCATGG  GCCAGTTTGA  GGGCACTGAC  ACCCTGgtga  agactgggca   8980
 Q M K G   F V Q       A V M       G Q F E     G T D       T L
                                   INTRON 6 (1255 bp)
aacaatagta acaggcactg  agccctgggc  cctccccact  ggccttttgca gTTTGCACTG  ATGCAGTACT   10240
                                                           F A L        M Q Y
CAAACCTCCT GAAGATCCAC  TTCACCTTCA  CCCAATTCCG  GACCAGCCCG  AGCCAGCAGA  GCCTGGTGGA   10310
 S N L L   K I H       F T F       T Q F R     T S P       S Q Q       S L V D
TCCCATCGTC CAACTGAAAG  GCCTGACGTT  CACGGCCACG  GGCATCCTGA  CAGTGGTgta  aagcaacccc   10380
 P I V     Q L K       G L T F     T A T       G I L       T V
gacccca    INTRON 7
```

SEQ ID NO: 4 (Also positions 1152 to 1176 of SEQ ID NO: 1)

SEQ ID NOS: 5 and 6
(SEQ ID NOS: 5 and 6 are collectively
positions 1095 to 1140 of SEQ ID NO: 1)

Sequence Range: -11390 to 10387
(SEQ ID NO:3)

FIGURE 9
Protein Sequence: SEQ ID NO: 2

Translational stop codon for CD11c

| | | | | | | -11321 |
|---|---|---|---|---|---|---|
| TGATCCCTCT | TTGCCTTGGA | CTTCTTCTCC | CGCGATTTTC | CCCACTTACT | TACCCTCACC | TGTCAGGCTG |
| | | | | | | -11251 |
| ACGGGGAGGA | ACCACTGCAC | CACCGAGAGA | GGCTGGGATG | GGCCTGCTTC | CTGTCTTTGG | GAGAAAACGT |
| | | | | | | -11181 |
| CTTGCTTGGG | AAGGGGCCTT | TGTCTTGTCA | AGGTTCCAAC | TGGAAACCCT | TAGGACAGGG | TCCCTGCTGT |
| | | | | | | -11111 |
| GTTCCCCAAA | AGGACTTGAC | TTCGAATTTC | TACCTAGAAA | TACATGGACA | ATACCCCCAG | GCCTCAGTCT |
| | | | | | | -11041 |
| CCCTTCTCCC | ATGAGGCACG | AATGATCTTT | CTTTCCTTTC | CTTTTTTTTT | TTTTTCTTTT | CTTTTTTTTT |
| | | | | | | -10971 |
| TTTTTTGAGA | CGGAGTCTCG | CTCTGTCACC | CAGGCTGGAG | TGCAATGGCG | TGATCTCGGC | TCGCTGCAAC |
| | | | | | | -10901 |
| CTCCGCCTCC | CGGGTTCAAG | TAATTCTGCT | GTCTCAGCCT | CCTGCGTAGC | TGGGACTACA | GGCACACGCC |
| | | | | | | -10831 |
| ACCTCGCCCG | GCCCGATCTT | TCTAAAATAC | AGTTCTGAAT | ATGCTGCTCA | TCCCCACCTG | TCTTCAACAG |
| | | | | | | -10761 |
| CTCCCCATTA | CCCTCAGGAC | AATGTCTGAA | CTCTCCAGCT | TCGCGTGAGA | AGTCCCCTTC | CATCCCAGAG |
| | | | | | | -10691 |
| GGTGGGCTTC | AGGGCGCACA | GCATGAGAGC | CTCTGTGCCC | CCATCACCCT | CGTTTCCAGT | GAATTAGTGT |
| | | | | | | -10621 |
| CATGTCAGCA | TCAGCTCAGG | GCTTCATCGT | GGGGCTCTCA | GTTCCGATTC | CCCAGGCTGA | ATTGGGAGTG |
| | | | | | | -10551 |
| AGATGCCTGC | ATGCTGGGTT | CTGCACAGCT | GGCCTCCCGC | GGTTGGGTCA | ACATTGCTGG | CCTGGAAGGG |
| | | | | | | -10481 |
| AGGAGCGCCC | TCTAGGGAGG | GACATGGCCC | CGGTGCGGCT | GCAGCTCACC | AGCCCCAGGG | GCAGAAGAGA |
| | | | | | | -10411 |
| CCCAACCACT | TCCTATTTTT | TGAGGCTATG | AATATAGTAC | CTGAAAAAAT | GCCAAGCACT | AGATTATTTT |
| | | | | | | -10341 |
| TTTAAAAAGC | GTACTTTAAA | TGTTTGTGTT | AATACACATT | AAAACATGCA | CAAAAAGATG | CATCTACCGC |
| | | | | | | -10271 |
| TCTTGGGAAA | TATGTCAAAG | GGTCTAAAAA | TAAAAAAGCC | TTCTGTGGAT | ATGAGTCCTG | AAGGATGACA |
| | | | | | | -10201 |
| CCCATGGGGT | CCCTTTACCA | CGGTGGACCC | TGGCCAGCAC | TGAGGCCTGG | GGCCAGGACA | AGAAGTTAAC |
| | | | | | | -10131 |
| CAGAGTAGGG | TTGTGAATAT | CCCTCTCTTG | GAAGTAACCT | GACCTCTTAA | TCTGCTCACT | CCACTCTCAG |

FIGURE 9 (continued)

```
                                                                        -10061
GGCTGGTGCC  GATGGTAAGC  TGGTGGAGCT  GTCGGGTGGA  GGGGGCATAG  AATAGAGAAG  GGACAACCTC
                                                                        -9991
CAGTGGCTAC  TTTTCCACCT  GGAAAGGTCT  CTGGAGTGAC  CAATACTCAC  AAGCGTTTCC  TACAAGTCCT
                                                                        -9921
AGGATGTGTT  GAAGGGCACA  CTGTCTGCAT  ATAGTGAGTG  ATTGAAGAAC  ATGTTGGGGT  CCCACATTGA
                                                                        -9851
GAGCTGCTGC  CCACAATAAG  GTCATTCTTG  CTATTATGCC  ACCATCCTGG  CATAAAGTTC  ATCATGGTGC
                                                                        -9781
TTGGCACTGA  GCTGGGGGCC  TCACAGGACA  AGCCATTCCT  GACCTCGGAG  TGACGCCACT  GCAGCTATCA
                                                                        -9711
CCAGCAAGGG  ACCCGGGCCG  TGTGGATGTT  TCAATTAGAA  AAACAGAAGG  GAGGCAGTTG  AGTGATTTGA
                                                                        -9641
AGGGAAGATG  GAAAGTGGCC  CTTTACCTCC  AGCCAAAAAT  GTCTGTCCTA  TACATCAGCA  GAGGCTCCAA
                                                                        -9571
AATCCCTGTG  GATTTGAAG   CTTTTGAGTC  CCCAGGATGA  CTAATTATTA  TGCAGTTTCC  TCAGAAAGGG
                                                                        -9501
AATCAGAAGA  TAAGGCTTTG  TAAGAATTCA  GCCCTAATGG  CTGGGCACAG  TGGCTCATGC  CTGTAATCCC
                                                                        -9431
AGCACTTTGG  GAGGCCGAGG  CAGGAGGATT  GTTTGTGCTC  AGAAATTTGA  GACCACCCTG  GGTAATATAT
                                                                        -9361
TCAAACCTTG  TGTCTACAAA  AAAATTTAAA  AATTACCCAG  GCATGGTGGC  ATGTGCTTGT  AGTCCCAGCT
                                                                        -9291
ACTTGGTAGG  CTGAAGCAGG  AGGATCACTT  GAGCCTGGGA  GGTTGAGGAT  ACAGTGAGCT  GTGATTTGGA
                                                                        -9221
CCACCACACT  CCAGCCTGGG  CAACAGAGAA  AGATCATGTC  TCAGAAAAAA  AAAAAAAAAT  TGACCCTAGA
                                                                        -9151
GTGGTGTTTC  TCAAAATGTG  TTCCACGAAC  CACTGGTGGT  CAATGATGGT  CTTCTAAGTG  GAAGGTTTTA
                                                                        -9081
GAGAAAAAGA  GCAAGAAACC  CATACATCTC  AAACATTTGA  AACTAGTGAT  TTGCACAGAA  ATAGTGTTGT
                                                                        -9011
GGCCTTAATA  ATTGTGTGGC  ACACGGACTC  CAGGGACTAC  AGTGGGTTCT  TGTCTAAATT  CAGGCAACAA
                                                                        -8941
GTTGTTATTT  TCTATTTTAT  TTTATTATTA  TTATTTTTG   AGATAGTCTC  ACTTTGTCTC  CCGGGCTGGA
                                                                        -8871
GTGTAGTGGC  ACGATCTCGG  CTCAACGCAA  CCTCTGTCTC  CTGGGTTCAA  GTGATGCCTC  TGCCTCAGCC
                                                                        -8801
TCCCAAGTAG  CTGGGAGTAC  AGGGGCGTAC  CACCATGCCC  ATTTTATTT   ATTTATTTTT  GAGACAGAGT
```

FIGURE 9 (continued)

```
CTCGCTCTGT  CACCCAGGCT  GGAGTGCAGT  GGCATGATCT  TGGCTCACTG  CAACCTCCGC  CTCCCAGGTT  -8731
CAAGTTCAAG  CGATTCTCCT  GCCTCAGCCT  CTGGAGTAGC  TGGGATTACA  GGCAGGCACC  ACCATTTCCA  -8661
GCTAATTTTT  GTATTTTTAG  TATAGATGGG  GTTTCACCAT  GTTGACTAGG  CTGGTCTCGA  ACTCCTGACC  -8591
TCATGATCCG  CCCTCCTCGG  CCTCCGAAAG  TGCTGGGATT  AGAGGTATGA  GCCACTGTAC  TTGGCCGACA  -8521
AGGTGTTATT  TTCTGATATT  CTTCCTTTGT  GTGTTATTGT  GTACATTTGT  TACATTTGCA  TTTTCAGGGT  -8451
TGGCTATTGT  GTTGCATTAG  ATCCCCGAAT  CACAAAATGG  ATCAATGGCT  CAAAAGCATG  GAAGTTGTGA  -8381
TTAAAAACTA  ATCTAATTGC  TACAATTTAC  AATAATGTCA  TCAAAGTCAA  TATTGACTTT  TAAATATTGA  -8311
GCCCAGTGCA  CGTATAGTAT  AGACATGCAT  ACCGGAATAA  GTGATTGTGA  GCCAAAACCC  GAAAATATCT  -8241
AGAAGGTATT  ATACTCCCTG  ACAGGTAGGT  TGTATTGGTT  CTGACATGTA  TTTGTCCCTA  GTGTGCTGCC  -8171
CATTCTGAAA  CTTTATCAAA  CAGTCGCATG  AACCTCTGAA  AGCTTTTGTG  TTATTTTCTT  ATTTATTTAT  -8101
TTATTGAGAT  GGAGTCTTGC  TCTGTCGCCC  AGGCTGGAGT  GCAGTGGCAT  CATCTTGGCT  CACTGCAACC  -8031
TTTGCCTCCT  GGGTTCAAGT  GATTCTCCTG  CCTCAGCCTC  TTGAGTAGCT  GGGATTACAG  GCGCGCACCA  -7961
CCACGCCCAG  CTAATTTTTG  TATTTTTAGT  ATAGACGGGG  GTTTCACCAT  GTTGGTCAGG  CTGGTCTCGA  -7891
ACCCCTGACC  TCATGATCTG  CCTGCCTCAG  GTAAAGCAAT  AGAGATTCTT  AGAACAACTG  CTACATGTAG  -7821
CTTTCCTATT  CAAAAGTGAT  TAGTGTTGTC  ACCGAATACA  GAGGAGACAG  CAAAACCACA  GTGACATAAA  -7751
TCAAAGGTGC  TTTTTAAAGT  AGCAAAAGTA  GGTACAAGTC  ACATAATTTC  CAAGAAGCTT  GTAGAAATGG  -7681
CAGTAGAGTT  CATACCTGCT  ATTGAAAGGT  TGCTTTTGGC  TGCAAATAAT  AGAAAAAAAC  AAAAGCATGT  -7611
AAGAGCAGAC  AGAAGACCTT  TACTCTGCAA  GAGGTTCAGG  TGCAGGTTAG  TGTTTAATGC  AGAGTCTCAG  -7541
CATTGACAGA  TTCTTTCTCA  TCTTCCAATT  GATCGTCCTT  GCGGGGGCGG  TTTAGTTCTT  TCCCACTGAC  -7471
```

FIGURE 9 (continued)

```
                                                                              -7401
TAGGATTGGG  TCAAATTCCA  TCCCCTTGGT  TGCATGCAGT  GCTGAGAAGG  TGAGCATGTG  CTTTTCACAG
                                                                              -7331
GCTTAATAAA  AAGAGGTAGC  TCCAGCCAGG  TGCAGTGACT  CATGCCTATA  ATCTCAGCAC  TTTGGGAGGC
                                                                              -7261
AGAGGTGGGT  AGGTCACCTG  AGGTCAGGAG  ATTGAGAACC  AGCCTGACCA  ACATGGCAAA  ACTCTGTCTC
                                                                              -7191
TACCGAAAAT  ACAAAAATTA  GCTGGGCATG  GTGGCAGGTG  CCTGTAATCC  CAGCTACTTG  GGAGGCTGAG
                                                                              -7121
GCAGGAGAAT  CGCTTGAACC  TGAGAGGTGG  AAGTTACAGT  GAGCTGAGGT  CATGCCACTT  GCACTCCAGC
                                                                              -7051
CTGGGGGACA  GAGTAGAACT  CTGTCTCAAC  AAAAAAAAAA  AAAAAAAGAG  AAAAAAAAAG  GAGGGTAGCT
                                                                              -6981
CCACCAGCCA  GGAAGGTGGC  AGCGCTGGTG  GCTGTTGGAT  AGGCTACCTA  CAGTGTCTGG  CAAATACTAT
                                                                              -6911
GCTTGAAGAC  TATGCTGTGA  GCAAGATTCC  TTTGTGAAGG  AACAGCTTGG  ACATTGTGTA  TGTCAGAGGT
                                                                              -6841
ATACAGCAGA  ATAGCAGTGA  CTAACGCTTG  TGTGGGAGAG  CAAGCATGTC  ACCTCATACT  TGGAATAACT
                                                                              -6771
CACTGCCATA  CAAAGTCTGA  ATCAGCTTTC  GTCTTTGTGC  AACACATGTA  TGTGGGAGCT  TTTCAGCTGC
                                                                              -6701
TGAAACCTCT  AGTGACAGAA  AAGGAGGTTT  TGTTGTTCAT  TTGTAATTAA  TGTTAATCCT  ATGAGTGGTG
                                                                              -6631
GGAGAGATAG  TGAGGTAGGA  GATCAGCAGG  ACCTGTTTTC  TGGTCACAAC  CCAGCTAATC  AGAGCATGAT
                                                                              -6561
CTGGTCAAGA  TGGGATGCAC  TAAAAAAACA  GCCCAAACCA  GCAGATGGCC  AGGAAAGCAA  ACTCTCATTA
                                                                              -6491
CCCTCGCCAC  TTATTAGCAT  AAAGACACTC  CCACCGGTGC  CATGACAGTT  TACAAATGCC  ATGGAAACAC
                                                                              -6421
ACCATAGCAA  CGGTCAGCAA  GTTACCTCAT  ATGGTTCTGG  AAACTCCCCA  CACCTTTTCC  AGATAGTTCT
                                                                              -6351
GAATAACCCA  CCCCTTAATT  TGCATGTAAT  TAAAAGTCGG  TATAAGTACA  GTTAGCCAGC  AGCCCACTGG
                                                                              -6281
CTGCTACTGT  GGGCTCACTG  CCTATGGGTT  GTCCTGCTCT  GCAAGGAACA  GCTACCTTGC  TGCCACTGCT
                                                                              -6211
GCTTCAATAA  ACCTGCTTTC  TTCCACCACA  GGCTCGCTCT  TCAGTTCTTT  CCTGAGCAAA  GTTAAGAACC
                                                                              -6141
CTCCCGGGCT  AAGCCCCAAT  TTTGGAGCTT  GCCTGCCCTG  CATCAGTAGA  ATGGGCTAAC  TACTTACGGT
```

FIGURE 9 (continued)

```
                                                                       -6071
GCACTCAGGC  TAAAGAGGCT  GATGCTTGCA  GGGCAGTATT  CACAGAGCAC  ACGGTAGTTC  ACGGGATGCC
                                                                       -6001
TCTCACCCTT  GACTCAGTGC  TTAAGAAAGG  AGGGAAAATG  GTGAACATGA  TCAAATCATG  GCCATTGCCT
                                                                       -5931
ATTCATCTTT  TCAGTGTTGT  ATGGAGGAAT  AGGCAAGTAG  GAGATTGCTT  TTCACATTAA  TGTCAAAGAG
                                                                       -5861
AAAGATAGTT  ACTTGGAACT  TAAAAAAATT  AATTGTGATA  AAATATACAT  AACATAAAAT  TTACCATCTT
                                                                       -5791
AACCATTTTT  AAGTATAGCC  AATCTCAAGA  GCTCTTTCTA  TCTTGTAAAA  CTGAAACCCT  ATACCCATTA
                                                                       -5721
AACAACTCCC  AATTCTCCCC  TTTCCCTAAC  TCCTGGCAAC  CACAATTCTT  TCTGTCTCTA  TGAATTTGAC
                                                                       -5651
TGCTTTGGCA  TGTCATAGAA  ATAGACTCAT  ACAGCATTTG  TCTTTTTGCG  ACTGGCATAT  TTTGCTTAGC
                                                                       -5581
ATAATGTCCT  CAAGGTTCAC  CCATGTGGTA  GCATGTGTCA  GAATTCCTCT  CCTTTTGAAG  GCTGAATAAT
                                                                       -5511
ATTCCATTGT  GTGTATATAC  CACGTTTTGT  TTATCCATTT  GCCCATCAAT  GGGCATTTGG  GTTGCTTTTT
                                                                       -5441
TTGCCTCTCA  TGAATGATGA  ATATGGGCGC  ACAAATATCT  CTTCAAGACC  ATGCTTTCAA  TTCTCTTGGG
                                                                       -5371
TATACACCCA  GAAGTGGAAT  TGCTGAATCA  TATGGTAATT  TTTTTTTTTT  TTTGAGACAG  AATCTTGCTC
                                                                       -5301
TGTTGCCCAG  GCTGGAGTGC  AGTGGCACAA  TCAGAGCTCA  CTGCAGCCTT  GGTCTTCTGG  GCTCAAGCGA
                                                                       -5231
TCCTCTTGCT  TCAGCCTTCC  GAGCTTCTGG  GACTAAAGGT  GTGTGCCATC  ATGCCTGGCT  AATGTTTTAA
                                                                       -5161
AAACGTTGCC  AGGCATGGTC  GCTCGTGCTT  GTAATCCTAG  CACTTTGGGA  AGCTGAGGCA  GGTGGATCCC
                                                                       -5091
CTGAGGTCAG  GAGTTTGAGA  CCAGCCTTGC  CAACATGGTG  AAATCCCGCC  TGTACTAAAA  ATACAAAAAT
                                                                       -5021
TAGCTGGGTG  TGGTGGCATG  TGCCTGTAGT  TCCAGCTACA  GGCAGGAGAA  TTGCTGGAAC  CTGGGTGGCA
                                                                       -4951
GAGGCTGCAG  TGAGCCGAGA  TTGCACCACT  GCACTCCAGC  CTGAGTGACA  GAGTGAGACT  CTGTCTCAAA
                                                                       -4881
AAAAAAAAAA  ATTTTAGAGA  TGGTGTCTCA  CTGTGTTGCC  CAGGCTGGTC  TTGAACTCCT  GCCCTAAAGT
                                                                       -4811
GATCCTCCTG  CTTCCGCCTC  CCAAAGTGCT  GGGATTACAG  GCATTAGCCA  CCATGCCTGG  CCTAGCTAAA
```

FIGURE 9 (continued)

```
                                                                         -4741
TTGTCTTTAA  TGTCGCATGT  CTGCAAAAAA  CACATCTATA  AAGCTAGAAA  AGTTGAGCAT  CCAACTTTTT
                                                                         -4671
ATGATTTAAC  TCTCATGACC  TGGCAATTTT  TCTAGCAAGG  AGCCTGGGCT  GGTGGTTTTA  GGAGAACTGA
                                                                         -4601
GTGAAAAAAA  GAAATACATT  AACTAGATTG  GATGCAAAGT  GCCTGCTGGT  CATGGGTGTT  TTCTGCTGGC
                                                                         -4531
CCCTGTTCAT  CTGTGCCTGT  TAGCCCACCC  ATGGGTGAGT  GGGGCAAAGT  GGCCAAACTG  ATTCTTAAGA
                                                                         -4461
GAGGCATACA  TGCAGAATCC  AAGTTAGTCA  TGATTTCGTT  TCTAGTCTGA  GTGAATGTGT  GTCCAGAATA
                                                                         -4391
TTTTATAAAC  TTTATCAGCT  CAGAGGGGAA  AACCTGTCTC  CATACTACGT  GGTTTATACA  AAGCTGTCAG
                                                                         -4321
GAATTCAGCA  TGATGAAGAA  ATGCACAAAA  CAAGTGTGAA  CAGATAAGTA  AAAGGATCTA  CTGAAAATCT
                                                                         -4251
TCAGGGTAGT  ATATTGTGTG  ACAGGACCAA  GAATTTGAAG  TCAACATCTG  TATTTGTGCC  CTCTGGACAA
                                                                         -4181
AGGTATTATC  CCTGATGATA  TAAAAATTAA  TTTTGGGCTG  GGTGTGGTGG  CTCATGCCTG  TAATCCCAGC
                                                                         -4111
ACTTTGGGAG  GCTGAGGAGG  GTGAATCGAC  TGACGTCAGG  AGTTGGAGGC  CAGCCTGTAT  CGACTAATAA
                                                                         -4041
TACAAAAAAA  TTAGCTGGAC  ATGGTGGCGT  GCACCTGTAA  TCCCAGCTAC  TCAGGAGGCT  GAGGTGGGAG
                                                                         -3971
AATTGCTTGA  ACTCGGGAGG  CCCAGGTTGC  AGTGAGTCGC  ACCACTGCAC  TCTAGCCTGG  GCGACAGAGT
                                                                         -3901
GAGACWCCGT  CTCAAAATAA  ACAAAATTAA  TTTCGAGGCC  AGGTGCAGTG  GCTCCAGGTG  CGGTGGTTCA
                                                                         -3831
TACCTGTAAT  TCCAGTGCTT  TAGGAGGCCA  GAGGATTGCT  TGAACCCAAC  AGTTCGAGAT  CAACCTGGGC
                                                                  -383
                                                                         -3761
AACATCAGTG  AGACTCCATC  TGTAGAAAAC  AATCAAACAG  ACAAACAACA  ACAACAAAAA  AACCAGAGGT
                                                                         -3691
GGGAGGATCA  CTTGAGCCCA  GGAGTCCGAG  GCTGCAGTGA  GCTATGGTCA  CGCCACTGCC  CTCTAGCTTG
                                                                         -3621
GGCAACAGTG  CCAGACTCTG  TCCTTAACAA  CAACAACAAC  AAAAATTAAT  TCTACTTTAA  CTGTCAGTTT
                                                                         -3551
CATGATATCC  TTCTATTAAG  AAAAACCTTT  TCTATCTGAT  GAACTATTGG  CTAGGTTTTC  TTTCTCTCTG
                                                                         -3481
CTTTTGACTA  ATGCATTTAA  TTACTTTCAT  TTGCAAACTC  TATCCTTCTC  ATCAACTTTG  TATTTTAGAT
```

FIGURE 9 (continued)

```
                                                                         -3411
GTGTCTATTG  ACAGCCTGGC  TTCCCTCAGC  GATCATTATG  ATGATCAAAG  TAGATGAATA  GGTAAAATTC
                                                                         -3341
AATGCAAATA  TTCCAGGGCA  TCTAAATCCA  TACCCCAAAT  GGGAAAAGGG  GAGAATTGGA  AGCCAGCAAT
                                                                         -3271
TTGAACACAT  TACTATGGAT  GTATTTTCT   CATGCGGGGG  AAAAAGTGAT  TTGGAGAGAG  AGAATTATGA
                                                                         -3201
ATGCATGTGA  AGAATAAAGC  CAAATTTCCT  GGGAGGAGGG  GAAGACCAGG  AGAAACAAAA  CCAAATCCTG
                                                                         -3131
GCTGTGGCCT  CTAAGGCATG  GGGACCTGGA  GTTATGCTCT  CCAGGCAGAC  ACAGCTCATT  CTGGAGAAAG
                                                                         -3061
GCTGCAAAAA  TATTCTCCTT  CACATTGATT  TGAAAACAAT  TATTAAATTC  TTGTTTTCTT  ATTTATCTAA
                                                                         -2991
GTGTAACTTT  TTAAAACTTA  CTGAGAGAAG  ACGGGCACGG  TGGCTCACTG  CTGTAATCCA  GTACTTTGGG
                                                                         -2921
AAGTCAAGGC  AGGTGGATCA  CCTATGGTCA  GGAGTTCGAG  ACCAGCCTGG  CCAATATGGC  AAAACCCCGT
                                                                         -2851
CTCTACTAAA  AATACAAAAA  TTATCAGGTG  TGGTGGTGTG  TGCCTGTAAT  CCCAGCTACT  CGGGAGGCTC
                                                                         -2781
AGACAGGAGA  ATCACTTGAA  CCTGGGAGGC  AGAGGTTGCA  ATGAGCTGAG  ATTGCACCAC  TGCACTCCAG
                                                                         -2711
CCTGGGCGAC  AGAGCAGGAC  TCCATCTCAA  AATAAAAATT  AATTGATTAA  TTAATTAAAA  ATTTACTGAG
                                                                         -2641
AGCTGGTGGT  TCCTTTAAGG  GTGGAGCCGC  CATCAAGTCC  CCAGAGGATG  CCCTGAATTT  GGGGGCATCA
                                                                         -2571
CCTTCAGCTG  CTGTGGACTC  TGAGCCTTGG  CAGCTCCAGC  TCCAGGCCTG  GGAGAAAGAT  GATTTCCTGG
                                                                         -2501
CAGCGTGCAG  TGATTGTGAG  CATTTGACTA  CCTTACTGCA  TTTTGCCCTT  ATCAKTGCTC  TCCAAACATG
                                                                         -2431
AGTGGAAAAC  AAAAAATTTT  GCTGAGACAA  GCGATAATAC  GAGTTAGGGA  AAGTTGGAGA  ATTTTATAGT
                                                                         -2361
TGCTGATATC  AGCAAATCGT  GAGTTTCAAG  CACTAACTTA  CAGAAGGAAG  TCCAAAATTA  AAGGGGATAT
                                                                         -2291
AGAAATGTGT  AAAAGATGAG  GTGTGGTGAA  GATGGAGAAA  ATGAAGAGCT  CTTTAAATTT  CTGAATTATG
                                                                         -2221
AAGAATCACC  AACAAATTAT  TTTGTGGTTC  CAAATACAGG  GAGAAGTTCA  CAGATCCACA  GAACTGATGA
                                                                         -2151
CAGGGTGCGG  CCAGCCACAA  ACCTTTCAGC  ACAAGAGGGA  GAAGGCTGCC  GCTCCACTTT  GCCTGGGCAG
```

FIGURE 9 (continued)

```
                                                                                    -2081
TCTTTGTAAG  GCAGTAGATA  AGTCAGCCTC  GAAGTTAGCA  ATCACAGCCC  TCGGCTCGGT  TTCCTGCAAG
                        -2052 N486
                             |————————————————————————————————————————————>
                                                                                    -2011
GGCATCGTTA  ATGCATCACA  ATTAATTTCT  TCTGTCCATT  AAATGTCAGC  TCTCAAGTAA  ATTGATGTAA

-1941
AATTTTTGTA  TAGAAAACTA  TTTCATATTA  TTTGCACTTG  ATGTTTAATT  ACATTTTAAA  TGTTTTGTTT

-1871
GTTTCATTTT  GTTTTGTTTT  TGAGACAGAG  TCTTGCTCTG  TTGCCCACGC  TGGAATGCAG  TGGTGTGATC

-1801
TTGACTCACT  GCAACCTCTG  CCTCCTGGGT  TTAAGCGATT  CTCCTGCCTC  AGCTTCCTGA  GTAGCTGGGA

-1731
TTACAGGCGT  GCACCACCAT  GCCTGGCTAA  TCTTTGTATT  TTTAGTAGAG  ATGGGGTTTC  ACCATGTTGG

-1661
CCAGGCTGGT  CCCGAACTCC  TGACCTCAAG  CTATACACYT  GCCTCAGCCT  CCCAAAGTGC  TGGAATTACA

-1591
GACATAAGCC  ACTGTGCCCA  GCCAAATGTT  TTAAATAATT  GTCACATATA  TATACAAAAT  AATTTATGTT

-1521
ATAGGTAGGG  ATCTTGTTAT  ATTTTAACCT  TCAAAGTATA  TTCCTAAGCT  TTTTATTTAT  TTTTTATTTT

-1451
TTATTTATTG  AGACAGTCTT  GCTCTGTCGC  CCAGGCTGGA  GTGCAGTGGC  GCAATCTCGA  CTCACTGCAA

-1381
ACTCTACCTC  CTGGGTTCAA  GCGATTCTCC  TGCCTCAGCC  TCCTGAGTAG  CTGGGATTAC  AGGTGCGCAC

-1311
CACCATGCCC  AGCTAATTTT  TGTATTTTTA  GTAGAGACGG  GGTTTCACCA  TATTGGCCAG  AGCTGGTCTC

-1241
AAACTCCTGA  CCTCAGGTGA  TCCATCCACC  TCAGCCTCTC  AAAGTGCTGG  GATTATAGGT  GTGAGCCACT

-1171
GCGCCTGGCC  TATTCCTAGC  CTTTTATATA  TAGACCTTTT  TCTTTTTCAC  ATTTTAAAGG  AACTTTTATG

-1101
TTTAATCATG  GAATATTTCA  AACATACAGA  AAAATCACAG  AAAATAAATA  ACAACCACTC  ATTTATCTTC

-1031
TCCCCAACCC  CATGTAATAA  ATATTAAAAT  ATTGTGTTAA  ATGCTAAATT  TAACACATGC  TAAAGGTTCC

-961
TGGCTGGATG  TGGTGGCTCA  CGCCTGTAAT  CCCAGTACTT  TGGGAGGAGG  AGGTGGGAGG  ATTGCTTGAG
                  N485
                   |————————————————————————————————————————————>
                                                                                    -891
TCCAGGAGCT  CGAGACCAGC  ATGGGCAACA  TAGTGCGATC  TCGTCTCTAC  AAAAAACAAA  AAAATTAGCT

-821
GGGCATGGTG  GTGTGCATCA  GTAATCCCAG  TGACTGGGAG  GCTGAGGTGG  GAGAATTGCT  TGAGTCTGGG
```

FIGURE 9 (continued)

```
                                                                                    -751
AATTTGAGGC  TGCAGTGAGC  CCTGATCATG  CCACTGCATT  CCAGCATGGG  CGACATAGCA  AAACTTGTCA
                                                                                    -681
AAAAAAAAAA  AAGTTTCCTC  TCTGCCCCAC  CATAGACAAC  CACTCTTCTG  ATTTCTATCT  TCGTAGAT68
                                    AP1
ATTTTGCCCA  TTCTCTTGTA  TATGAAAGAA  ACCAGACATT  AGGCATTCTG  GTGTCTGGTT  TCTTTCACTT
                                                                                    -611
                                                                                    -541
AAGATAAAAT  TGAGTTAACC  TGTATTGTTG  TACAGAACTG  CAGTTTGTTC  TTTGTTATTT  ATTGTAAAGA
                                                                                    -471
CAGGGTCTGG  CTATGTTGCC  TAGGCTGGTC  TCGAACTGTT  GGCCTCAAGC  AATCCACCTG  CCAAGCTCTG
                                                                                    -401
GGACCACAGG  CATGAGCCAT  GGCATCTGAT  CKGTAGTTTG  ATCTTATTTC  TTGCTGAGTA  GTAGCCCATG
    AP1                                                                             -331
GCATGACTTT  ATTATTTTGG  GTGTCCATTC  TCCTCTGGAG  GGGCTCTGCT  TTTTGAAACC  ACACCCTGGC
            Ets                                                                     -261
CTAGCTCCCC  TTCTCCCTGC  CTCTCTGCAG  GCTCACATCC  ACATGCCAAG  ACCTCTGCAG  CCATTCTGCT
    Ets                                                                             -191
TCCTGTCCTT  CCACTCCTGT  GGGACCTCAG  AGAGCTACGG  GGCTCCCTGG  GTACCAACTG  GCTCCTGAGG
    Sp1/Sp3                                                 Sp1/Sp3                 -121
CCTGGGGGAG  GGTGGTCTTC  TGGGAGAAGG  AAGCCAGGTC  CCTGCAGGTT  GTGGAGGGGG  ACAGAATGAG
                        Sp1/Sp3                                         Ets    -51
GGTTTTTCCC  CAGGATGTTG  TTGGCCCCTG  CCCCCACTTC  TGTTCCATAA  TTAACCACGC  CCCTCCTACC
                        Sp1/Sp3                             +1                      20
CACTGTGCCC  CTCTTCCTGC  TGTGTGGAGG  CCCTGAATCA  TTATTTTAAC  TACCCCCTGG  GAGGGTGAGC
    Ets                 Ets                                                         90
ACCTTCTGTG  CTCTGTCCCC  AACCTTCCAC  TTCCCCTCAA  CGCGCTGCTC  AGGGATGACC  TTCGGCACTG
                                                              M   T      F  G  T
                                                                                    160
TGCTTCTTCT  CAGTGGTAAG  TGGGGCCAGG  GTGCTGGGGA  GAAGCTTGGA  GGAGTTCTGA  GGGGACTCCA
 V  L  L     S  V
                                                                                    230
TCTGGGAGGG  CAGGCTGGGG  GCTGGTGGTC  GGCTCCAACC  ACTCTTATGA  GGAGCTGAGG  CAGGGGAGTG
                                                                                    300
CTTCATGTGC  GAGTGGCCCG  GAGTCAGTAG  AGTGTGACCT  GAATGAAGAG  GGGCTCAGGG  GCTGTGCTCA
                                                                                    370
GGTGGCGACT  AAGCTACCTC  TCCAGCTGGC  TATGTTGTCC  CAGGCTTCCC  TGCTCCCACT  CATGGAGTCC
                                                                                    440
CTGGTGTGGG  TGACAGAGGT  CTCCCCAGCC  TCCCCCGGGA  GTGGAAGGCC  ACAGAAGCCA  CCAGGGAGGG
                                                                                    510
GGAAAGGTTG  GACATCACCT  CCCTGGGCCT  NNNNNTTCCC  CCAAGTCCTG  ACTGCACGTA  GGGAAGAGGC
```

FIGURE 9 (continued)

```
                                                                            580
CCCCTGCTGA   AAACTGCATC   AGAGTCACAT   TCACGTGCCA   TCAAAAATCA   GGCTTGGCTG   GGTGCGGTGG
                                                                            650
CTCATGCTTA   TAATCCCAGC   ACTTTGGGAG   GCCGAGATGG   GCGTATCCCC   TGAGGTCAGC   AGTTTGTGAC
                                                                            720
CAGCCTGGCC   AACATGGTGA   AACCCCATCT   TTACCAAAAA   TATAAAAATT   AGCCGGGCAT   GGTGGCGTGC
                                                                            790
ACTTGTAATC   CCAGCTACTT   GGGAAGCTGA   GGCAAGAGAA   TCGCTTGAAC   CCAGGAGACG   GAAGTTGCAG
                                                                            860
TGAGCTGAGA   TCGTGCCGTT   GCACTCCAGC   CTCAGCAACA   GAGCGAGACT   CCATCTCAAA   AAAAAAAAA
                                                                            930
AAAAAAGAA    AAAAAAGAAA   AAGAGGCTGG   GAGGTCCTAG   GGATTGGGGC   TTCTTTAACT   CCCAGCCTCC
                                                                           1000
CCGCCCACCA   AATATTCCTC   AGTCCTGGCT   TCTTATCATG   GATTCAACCT   GGATGTGGAG   GAGCCTACGA
                          L  A        S  Y  H  G   F  N  L     D  V  E     E  P  T
                                                                           1070
TGTTCCAGGA   GGATGCAGGC   GGGTTTGGGC   AGAGCGTGGT   GCAGTTCGGT   GGATCTCGGT   AGGCCCCACT
I  F  Q  E   D  A  G     G  F  G  Q   S  V  V   .  Q  F  G     G  S  R
                                                                           1140
CACCCTCCTT   CCCCAACCTC   CACTACATCA   AGTCCTGTGG   ATGGGTACAC   GTGGGTTACC   CGAGGGAGGT
                                                                           1210
GTCCTGGAGG   AAGGCCAGCA   GGGGTGAGAA   GTCTTCCCTT   GGCTCCTTGG   AGGCCCTGAC   ATCAGCACCT
                                                                           1280
ATTATTCTCA   ATCCCAGGAA   AGGCCACAAA   ACTCTAGACA   AGACCCTACC   TTACCTCGGG   AGGGAAGCCT
                                                                           1350
TGAACCTGCC   TCCCAGGCAG   GGCCCACTTC   TTGGGGCCAG   TATGGTCACA   CAGGGCCCAC   ACTCATTAAC
                                                                           1420
TTTGGAGTTT   AATGTTCTGC   CCTTGACCTC   TTGAAATTCC   TGATTATTTT   TATTTTTATT   TTTACTCCAG
                                                                           1490
CTCTGTTACC   CAGGCTGGAG   TGCAGTGGTG   CAATCACAGC   TTACTGCAGC   CTCAAACTCT   CGGGCACAAG
                                                                           1560
TGATCCTCTC   ACCTCAGCCT   CCTGAATAGC   TGGGACCACA   GGTGCATGCC   ATCATGCCTG   TTTTTTGTTT
                                                                           1630
TGTTTTGTTT   TACTTTTTAC   AGAGATGGAG   TCTTGCTATG   TTGTCCAGAC   TGGCTGAACT   CCTGGGCTCA
                                                                           1700
AGCAATCCTC   CTGCCTTCGC   CTCCCAAAGT   GCTGGGATTA   CAGGTGTGAG   CCACCCTGTC   TTGCCAATTC
                                                                           1770
TTAAAAATTT   TATCTGTGCA   TTTGTGTTTT   GCAAGTAAAG   AATGATGGCA   GGGCTGGGCA   CCATGGCTCA
                                                                           1840
CGCCTATAAT   CCCAACSCTT   TGGGAGGCTG   AGGCGGGCAG   ATCATCTGAG   GCCAGGAGTT   TGAGACCAGT
```

FIGURE 9 (continued)

```
                                                                            1910
TTGGCCAACA  CAGCAAAACC  CCATCTCTAC  TAAAAATGCA  AAAAAAATTA  GCCGGGCATG  GTGGCAGGCA
                                                                            1980
TCTGTAATCC  CAGCTACTTG  GGAGGCTGAG  GCAGGAGAAT  CGCTTGAACC  TGGGAGGTGG  AGGTTGCAGT
                                                                            2050
GAGCCGAGAT  CGTGCCACTT  TACTCCAGCC  TAGGTGACAG  AGTGAGACTC  CGTCAAAAAA  AAAAAGTCAT
                                                                            2120
GGGAGAAGGG  AGATGTACTG  GGGGTTTGGA  GCCTTAGCTC  AGCAGCAGCC  CCACCTCCCA  CCGCCTCCTG
                                                                            2190
AAGGGTGGTG  AAGGGGTATC  AGCTGCTGGC  TCCCCCACCC  ATGTGGGAGC  AATGACCGCT  GCTACCTTCC
                                                                            2260
GCCCCTGGCA  TGAGCTGGGT  AAAGTCAGTT  AGGGGCGCTC  ACTCTGGGAG  TACCCCGAGG  GAGTGGGACA
                                                                            2330
CTACATAGCA  AATAAAAAAC  GTCAGGACAG  GTTGAGGAAA  GAGAGCAGAA  GAAAGGTAAG  AGCCCCCCAA
                                                                            2400
CCCCAAGAGA  CCCCACAGTT  TTATTTCAAA  TTGGGACCCA  CAAATTATGA  ACCTGCCCCC  ACTTCCAGGA
                                                                            2470
GCTCACATTC  TCCTGTCCCA  GAGAGTTCAA  GTCACAATGT  GACACAGGTG  TCACCAAGGT  CTGGGGGGCG
                                                                            2540
CAGGCAGGGA  GAGAGCAGAC  CCAGGAGGGT  TCCATGGAGG  AAGTGGTGCT  GGCAGTGAGC  CCCAGTGGAC
                                                                            2610
AGGAAGGCTC  AGTTGGTCAC  GAGGAGCTAT  AAGAGGTCAC  CGAGCTCCAA  CCGCGCACCC  CTCTCCCTTC
                                                                            2680
CTCATGTGAC  TGGCAGTCTG  GGGGATGGA   AGCAAGCACC  AGGCACCAGG  CTTTTGTTTT  TCTTTATTTG
                                                                            2750
CAAATGTGGT  CAACTGAGGT  GCACAAATCT  GAAAGACCCA  ATCTGATAAA  GGATACACAT  GTGCGTGCCT
                                                                            2820
GGGTGAGCCC  CACCTAGGTC  AGCTGCTCCA  GTGTCAAATC  CCACAGGCAC  AGGGCTGCCG  TGGACCCCTT
                                                                            2890
CTCATCACCC  AACATCCCCA  GAGAACCCCT  GGTCAGACTT  CTGTCACCAT  CAGTTTTTTG  GGCCACATTT
                                                                            2960
TAAAAAAAGA  ATACATTGGC  TGAGTGCAGT  GGCTTATGCC  TATAATCCTA  GAACTTTGGG  AGGCTGAGGC
                                                                            3030
GGGTGGATCA  CCTAAGGTCA  AGAGTTCAAG  ACCAGCCTGA  CCAATATGGT  GAAACCCTGT  CTCTACTAAA
                                                                            3100
AAATACAAAA  ATTAGCCTGG  CGTGATGGCA  GGTGCCTGTA  ATCCCAGCTA  GCTGGGTGAC  TGAAATAGGA
                                                                            3170
GATTTGCTTG  AACCTGGGAG  GTGGAGGTTG  CAGTGAGCTG  AGATCACGCC  ATTGCACTCC  AACCTGGGTG
```

FIGURE 9 (continued)

```
ACAGAGTGAA  ACTCTGTCTC  AAAAAACATA  TGGGTTGATG  GGTTACACTA  AAGTTTTGCT  CATCGTTTGT  3240
ATCAGCAGGT  TCCAAACTGC  TACCTCTCTA  GCCAATGCTC  AGATTTTCTT  CACAAAGCCT  TAGGCATCCC  3310
CTGAATCATG  ATGCACAGGG  ATTGTAGCTT  TCTGTAAAGG  AGCGGCACCT  AGAAGGAACC  CTCACATGGC  3380
CATTTAATGA  AGCCTTGCTT  GGCGCATTAA  AATACACCAG  ATATCTGTCTG CTTTTCTCAC  AGACAGGAGA  3450
TTGTGGGTAG  TGAGAAAACA  TTTCCAAAAT  TAAAAAACTT  TCCCACTCAG  GGAGTTTTGC  AAATAAACCC  3520
TTGACTCTAC  ATAACTATAG  ATATAGTTAT  GGATCCTAGT  ACACTGCTTT  ACATTGGCCA  ATTGAAATTG  3590
CTTATACAAT  ATTTAAATTG  GTCCAATGAA  TTACAGAATC  AACTATTTGT  TTTGAAAGCA  CATGTCTTCA  3660
GGAAATTGTT  CCAATTAACT  TGAGATGATC  TTATTTCTTG  GGTGGTTCAA  AATAATGGCA  ACTCAGAAAC  3730
GCAATGTGCT  TACCCATGAT  TGGGAAATGC  CATTTGGTC   TTTAAATAGG  TCTTTTTTTT  TTTTTTTTT   3800
TTTTTTTTT   GGTGAATGTT  AAAAGAAAT   TTCTAAACAT  AAATACACAC  ATACGTACTT  ATGCACACTC  3870
AAAACCAAAT  AAACCCCAGC  ATGGCCCCTG  GGCATCTGTG  AGTTACACTT  GGGCCCTGAT  TTCTGAATAT  3940
TCTGCCAAGT  GGCAAATGCC  AGGAATTTCC  CCCACAGAGT  CTCGCTTCCC  CATGGAGGGA  CACTTCCTCA  4010
CCCCCAAGTG  CCCGCTGCTC  CCACCCCTCC  TGTGGCTGCA  GTGACATGGC  CATGGTTGTG  TCTCCAGACT  4080
                                                                             L
GTGGTGGGA | GCACCCCTGG  AGGTGGTGGC  GGCCAACCAG | ACGGGACGGC  TGTATGACTG  GGCAGCTGCC| 4150
 V  V  G     A  P  L    E  V  V  A    A  N  Q    T  G  R     L  Y  D  C    A  A  A
ACGGGCATGT  GCCAGCCCAT  CCCGCTGCAC| AGTGAGTGAC  CACCTGGGAA  TTGGGCCCCT  CAACCCTCCT  4220
 T  G  M  C    Q  P  I    P  L  H  I
                                    Intron 3
GGACCCAACT  GTGCCCCCGC  TTAGCTTCCA  GTCCAGACCT  TCCCCGCAAA  TGAGTGTGTG  CTGTGAGTGA  4290
GACCCCGCGT  GTCTGCCCTT  GCAGTCCGC   CTGAGCCCGT  GAACATGTCC  TTGGGCCTGA  CCCTGGCAGC  4360
                          R  P       E  A  V    N  M  S    L  G  L      T  L  A  A
CTCGACCAAC| GGCTCGCGGC  TCCTGGTGAG  TGAGTGTCTT  GGGCCACGGG  GGGGTGGGGT  GGGGCGGGGG  4430
 S  T  N    G  S  R     L  L
GTGTTGTTGG  GGAGGAGGCT  GGGGCTGGGA  GTGAAGGAGG  AGGGGCTGCT  AGGGACTCCT  GGCTCACAGG  4500
                     Intron 4
```

FIGURE 9 (continued)

```
                                                                             4570
CTTCTGCCTC  CAGGCCTGTG  GCCCGACCCT  GCACAGAGTC  TGTGGGGAGA  ACTCATACTC  AAAGGGTTCC
              A  C       G  P  T  L    H  R  V    C  G  E    N  S  Y  S    K  G  S
                                                                             4640(1700)
TGCCTCCTGC  TGGGCTCGCG  CTGGGAGATC  ATCCAGACAG  TCCCCGACGC  CACGCCAGGT  AGGTCCCTGG  Intron
 C  L  L     L  G  S  R    W  E  I    I  Q  T     V  P  D  A    T  P  E                5
                                                                                    (4267)
CAGGCCATGG  TTCCCTGTGG  AGCACATGCT  GGCACTGAGG  GTGAGCAGGC  GTGAGGCCTG  TGTCTGGGCC  4710

4780
CCTGTGCCCT  CCCTGGAGGG  CCGAGTGTGG  CTAGGAGAGA  AGCCAGGAGA  AGAGGGTGGC  TCAGGCAGGA

4850
GCCCTGCTGC  TCCAGGGTAG  AAGTTCTTTG  CAGGGTTTTT  CTTTATATTT  TTTTCTTTTT  AAGACAGGGT

4920
CCCTGCCAGG  CACAGTGGCT  CAGGCCTGTA  ATTCCAGCAT  TTTAGGAGGC  TGAGGTGGGC  GGGATCACCT

4990
GAGGTCAGGA  GTTCGAGACC  AGCCTGGCCA  ATGTGGTGAA  ACCCCTCTAC  TAAAAATACA  AAACAAAACA

5060
AAACAAAATA  GCAGGATGTG  GTGGTGTGCG  CCTGTAATCC  CAGCCACTCG  GGTAGGCAGA  GACAGAAGAA

5130
TCGCTTGAAC  CCAGGAGGCG  GAGGTTGCAG  TGAGCTGAGA  TTGTGCCATT  GCACTCCAGC  CTGGGTGACA

5200
AGAGCAAAAC  TCCATCTCAA  AAAAAAAAAA  AAAACAAAAA  ACAGAGTTTC  TGTCAGGCTG  CATGCACCAC

5270
CACACCCTGC  TAATTTTTTT  GAGACAGAGT  CTTGCTCTGT  CGCCCAGGCT  GGAGTGCAGT  GGTGCAATCA

5340
TAGCTCACTG  CAGCCTCGAA  CTCCTGGGCT  CAAGTGATCC  TCCTCCCTTA  GCCTACTGAG  TAGTTGGGAC

5410
TGCAGGTACA  TGCATCACAC  CTGGCTAATT  AAAAAAAATG  TTTTTGTAGA  AATGGGGGTC  TTGCTATGTT

5480
ACCCAGCCTG  GTCTTGAACT  CCTGGGCTCA  AGTAATCCTC  TGCCACAGCC  TCTCAAAGTG  TTGGGATGAC

5550
AGGCATGAGT  CCTTGTGCCT  GGCCTGAGGG  ATGAAAGTTC  TGATGGAGGC  AGAGAGGAGC  CCCACTGTGC

5620
GGGCTGTAGA  GGGCACAGCA  TCTTCCAGTT  GCCAACAGGT  GCATGGCCAC  TTCTTGAGTT  TCAGAGGAAG

5690
GACCTTAGTG  TGGTAAAGAA  CGTGGTGAGG  AAGATAAATC  CATGAGGGAG  GTGTTTCTTC  TGGATGGTTC

5760
ACTGCTGAGC  TTCCAGGATT  CCCCAAACTA  ACTTTCCTCT  CGAAGAGGAG  CAAATGACAG  GGCTGCGGAA

5830
AATGCGATGT  GCAATTTTGT  CAGTGCCCAT  GTCTTCCACA  GAGAACAGGG  CCTGGGACA   CCACCATGAC
```

FIGURE 9 (continued)

```
                                                                        5900
ATCTCTCTGA  GGGTTGGTCT  GCATCATGGT  GGTTCCCAAG  TTTGTTTTCC  ATGGGCACCA  GGCTTCATTC
                                                                        5970
CCTTGAAGCT  TCATTCCCTC  AAAGCCATTC  AGTTTCCTCA  TTGGTAAAAT  AGAGCTCAAT  AATCAGGGGG
                                                                        6040
TTATGAAGGT  GAAAGGGATT  GAGGTGCATA  AAGCACTTGG  AACCCTGCCT  GGCACATAGT  ATGTGATAGC
                                                                        6110
CCCTCTGACC  CATCTTCCAG  CTGGGGACTG  CATGCTGGGA  CTGGAGGAA   GATACAGGCA  AACTGTCTCA
                                                                        6180
TCTGCCGTGT  GAGAGGGAAT  GCCAGGGGCC  GCTCAGGGTG  CTGACCGAGG  GTGGGCTTC   AGACCAGAGA
                                                                        6250
GGCCATGATG  ACAGGCATGC  TGGGCCTTTA  GACAAAGGTG  GAGCAGCAGC  AGAAACATTA  CCAGAGCAAA
                                                                        6320
TGGTGAGGGT  GGAGTCTATG  GAGGGGACCA  AGGGAAGGGG  GAAGGGACAT  CCAGGGTTCT  TGGGGGGACC
                                                                        6390
GTGCCCAGCC  TGAGATGTCT  GTGAAGCTAG  GTTAGGGAGG  TGGCACTTAA  AAACAAGGGG  TAAATGCTTT
                                                                        6460
CTCACAGCCA  TCCGTGGAAC  TCATGAGGTG  GGATGCCTGA  TGCAAATGGG  ACTGGAGCAC  AAAACTGGTG
                                                                        6530
CAGGCAAGGG  GGGTGTGGGT  CCAAGTAGAA  GGGACCAGGG  TCCACTGAGG  ATCACCTGTG  TGCCAAGCAG
                                                                        6600
TGCTGAATAC  CTGGTATGAA  TCACCTTATT  GCATCCTCAC  AACATCCTGG  GTGGTGGGCA  GGCCCATTCT
                                                                        6670
CATTTTACAG  ATATGAAAAC  CAAGGTTCAG  ATAGATGAGT  TCCATCGATA  GCAAGAGGCA  GAGCCCAGAG
                                                                        6740
CTTGAGCCAT  CCTTGCCTGA  TTGGTGGGGT  CCTTTTTCAA  AAGGATAAGT  CCAGGCTTCT  GCTAGTGGGA
                                                                        6810
GACCAGGGGA  TACAATAAAA  AGACCAAGAA  ACAGAAGAGA  CATTGTGAGA  GGATTTGCCA  CAGACCTGGC
                                                                        6880
CTGAGAGAGG  ATGAGAGGGT  GGTTTCTTGA  CGCAGCTGAA  AAAACAGGCA  CCACTGCAAG  ATGTTGGCTG
                                                                        6950
CCCAGATGTG  GGCAAAAAAC  GGGGAGCTCC  TGGGGGGATC  TGCAGCCTGC  CCCATGGATG  TCAAGATTTG
                                                                        7020
CTGGTGATTG  AAGAAGCAGG  AAGGAAGTGA  CCTTCTGTTT  CTCCCCAGCA  CCCTTGAAGC  ACCAGTGGTT
                                                                        7090
GAGCAAGTGG  GGTAGGGGAG  AGGAAAGAGG  AAAAGGCATT  TTTTTTTTCT  GCAGTGGTGG  GCAGGGGGCA
                                                                        7160
GAAACCACAG  CCCTGTGGTG  TGGGCCTCAC  ACCTTAGTGC  TCTGGTGGCC  TGATCTCCCA  GTGCCCTGCG
```

FIGURE 9 (continued)

```
                                                                              7230
GGCAGCACAG  GATGTGGCTG  CTGGTGGAGG  TACCAACTGG  GCCCTGAACA  CAGGCCACAC  ACCCCCCATG
                                                                              7300
AGCCTGGGGA  CAGCATGAAA  AGTCTTATTT  GTTCATGTGG  ATATGATGTG  CCCTCACGAT  TGCAGAGTGA
                                                                              7370
ACTCCACAAA  CTCTGAGGTA  ACTTGGGAAT  GTTCTTTTTT  TTTGAGACGG  AGTCTCACTC  TGTCGCCCAG
                                                                              7440
GCTGGAGTGC  AGTGGCACAA  TCTTGGCTCA  CTGCAGCCTC  CACCTCCCAG  GTTCAAGTGA  TTCTCCTGCC
                                                                              7510
TCAGCCCCCC  AAATAGCTAG  GATTACAGGC  ACCGCCACCA  TGCCGGGCTA  ATTTTTTTGT  ATTTTTAGTA
                                                                              7580
GAGATGGGGT  TTCACCATGT  TGGCCAGGCT  GGTTTTGAAC  TCCTGACCTC  AAGTAATCCG  CCCACCTCAG
                                                                              7650
CGTCCCAAAG  TGCTAGGATT  ACAGGCGTGA  GCCACCACTC  CCAACTGGGA  ATATTCTTGG  GCACCGCACC
                                                                              7720
CATGGGAGCA  TGAAGGGTGG  ATGCAATGCA  ATCATAACAG  AGGCCCAAGG  TCAGCACTGG  GGTGCTTGCC
                                                                              7790
TGTCATCCCA  GTGCTTTGGG  AGGCCGAGGT  GAGTGGATCG  TTAGAGCCCA  GGAGGTTGAG  ACCAGCCTGG
                                                                              7860
GCAACATGGC  GAAACTCCCT  CTCTACAAAA  AGATACAAAA  ATTAGCCAGG  CAAGGTGGTG  CACACCTGTA
                                                                              7930
GTCCCAGCTA  CTCAGGAGAC  TGAGGTGGGA  GAATTGCCTG  AGCCTGGGGA  GGTCGAGGCT  GCACTGACCT
                                                                              8000
GTGATCACAC  CACCACACTC  CAGCCTGGGT  GACAGTGAGA  CTCTGCCTCA  AAAAAACAAA  AAATGAAAAA
                                                                              8070
ACCAGAGGCC  TCAGCCAATG  CCTGGGGGGC  TCAGAGTGCA  GCTGGCCCTT  CAGACGCTGA  ACCAGTCATC
                                                                              8140
GGTAAAGGTT  TCCTCCAGGG  GCAGGAGGTG  TCCCAGTGGG  CAACAGTTCC  CCTCTGCCTA  GCGTGATTCC
                                                                              8210
TGGGAAGGGA  CTCAGCTCAG  AGCCAACTCC  ACGTAGCTGG  AAATAAGGAC  CTCTGACCGA  CTGGGGGTAG
                                                                              8280
GGTGGGGTCT  GGGGTGGATC  CCTGCCCCAC  CCCCACAGCA  TCCCTACAGG  CATATCCTAC  AGGCCTCGAA
                                                                              8350
GGTGCCTGGC  ACGTGGTGAG  AATGGTGCCA  GCGGCTGACC  CTGGCAGAGG  GCCAGGACTT  GTCTCCAGCA
                                                                              8420
CCCATGTGCG  TGTTGCTTTA  TCCTTGCAGT  GATCCCACGT  GGTAGCCACT  GATATTACCT  TCATTTTACA
                                                                              8490
GATAGGGACA  CTGAAGTCCA  GAGAAGTTAA  GTAATGTGCC  TGAATTCACC  AATTAGCACG  TGGCTGAGCT
```

FIGURE 9 (continued)

```
                                                                                  8560
TATATTATTT  GTAGGGCTTC  AAAACACATG  GGAAATGGTT  TGTAAATCCA  AAATAATTCC  AAAATAAAGT
                                                                                  9960
TTATTAAAAC  TGAAAACAAT  ATGGCTTGGT  GTGGTGGCTC  ACACCTGTAA  TCCCAGCACT  TTGGGAGGCT
                                                                                 10030
NGAGGTGGGA  GTATTGCTTG  AGGCCAAGAG  TTCGAGACCA  GCCTGGGCAA  CATAGTGAGA  CCTTGTCTCT
                                                                                 10100
ACCAAAAACA  AAACAAAACA  AAAAACAAAG  CCAGGCATGT  GACGTGTGCC  TGTAGTTCCA  GCTACTTGGA
                                                                                 10170
GGCTGAGGCA  GGAGGATCAC  TTGAGGCCAG  GAGTTTGAGA  GACCCTGTCT  CTACAAAAAA  TTAAAATAAA
                                                                                 10240
AACAATAGTA  ACAGGCACTG  AGCCCTGGGC  CCTCCCCACT  GGCCTTTGCA  GTTTGCACTG  ATGCAGTACT
                                                             F  A  L    M  Q  Y
                                                                                 10310
CAAACCTCCT  GAAGATCCAC  TTCACCTTCA  CCCAATTCCG  GACCAGCCCG  AGCCAGCAGA  GCCTGGTGGA
S  N  L  L  K  I  H    F  T  F  T  Q  F  R    T  S  P    S  Q  Q  S    L  V  D
                                                                                 10380
TCCCATCGTC  CAACTGAAAG  GCCTGACGTT  CACGGCCACG  GGCATCCTGA  CAGTGGTGTA  AAGCAACCCC
P  I  V    Q  L  K    G  L  T  F    T  A  T    G  I  L  T    V
GACCCCA...Intron 7
```

MYELOID CELL PROMOTER AND CONSTRUCTS CONTAINING SAME

TECHNICAL FIELD

The present invention relates to a novel promoter isolated from a myeloid cell, as well as cis-acting elements from the myeloid cell, and to novel constructs containing the same.

BACKGROUND OF THE INVENTION

The expression of foreign genes in various cell types has become a commonplace occurrence in the field of biotechnology. The expression of the foreign, or heterologous, gene is performed by the transcription of the genetic information in the gene from DNA to RNA. The RNA is then translated into the protein for which the gene encodes.

In transcription, the RNA is synthesized using the DNA of the gene for a template. The RNA is synthesized by a reaction catalyzed by RNA polymerases. The RNA polymerase binds to a particular molecular site on the DNA to initiate the transcription process. This site to which the RNA polymerase binds is known as the promoter.

Therefore, in order to express heterologous genes in foreign cells, the genes must be under the control of a promoter. Although numerous promoters for expressing foreign genes have been taught in the literature, these promoters have generally failed to function when used to express genes within myeloid cells. Therefore, a need exists for promoters which may be used to express genes within such cells.

Integrins are a large family of cell surface glycoproteins that are heterodimers comprised of α and β chain subunits. The promoters of integrins are of special interest as these promoters may be used to express genes in a myeloid-specific manner. This is especially useful, as typical promoters which are used in genetic research, such as retroviral promoters, become repressed after being introduced into myeloid cells.

Genes linked to myeloid specific promoters may be used in a wide variety of applications. These applications include use in the development of cancer vaccines, as well as being used for screening compounds for their effect on myeloid cell specific gene expression.

A need therefore remains for the identification and isolation of myeloid cell specific promoters.

SUMMARY OF THE INVENTION

The present invention relates to myeloid cell specific gene expression. The invention includes myeloid cell specific gene expression under the control of a myeloid cell specific promoter, preferably the CD11d promoter.

A preferred myeloid cell specific promoter is all or a functional portion of isolated or recombinant SEQ ID NO:1, such that the sequence is sufficient to direct myeloid cell specific expression of a gene. More preferably, the myeloid cell specific promoter of the present invention is the −946 to +74 region in FIG. 1 that is upstream (5') of the CD11d gene, as identified by positions 225 to 1244 of SEQ ID NO:1. In particular, the present invention relates to portions of this sequence that are sufficient to direct myeloid cell specific expression of a heterologous gene, and also includes modifications of this sequence that retain sufficient activity to direct myeloid cell specific expression of a heterologous gene. More preferably, the invention relates to the region from −173 to +74 that is upstream (5') of the CD11d gene in FIG. 1 (positions 998 to 1244 of SEQ ID NO:1). The invention further includes all or a functional portion of isolated or recombinant SEQ ID NO:1, wherein the sequence comprises one or more modifications, such that the modified sequence retains sufficient activity to direct myeloid cell specific expression of a gene.

The invention further relates to a cis-acting element that influences the activity of the myeloid cell specific promoter. This influence may be either to increase or decrease the activity of the myeloid cell specific promoter. The cis-acting element comprises a portion of SEQ ID NO:1 that is sufficient to influence the activity of the myeloid cell specific promoter. In particular, the present invention relates to portions of this sequence that are sufficient to function as a cis-acting element that influences the activity of the myeloid cell specific promoter, and also includes modifications of this element that retain sufficient activity to influence the activity of the myeloid cell specific promoter.

A preferred cis-acting element is the −173 to +74 region that is upstream (5') of the CD11d gene as shown in FIG. 1 (positions 998 to 1244 of SEQ ID NO:1). Also preferred is the −72 to −40 region (positions 1099 to 1131 of SEQ ID NO:1), more specifically, the −63 to −40 region (positions 1108 to 1131 of SEQ ID NO:1), that is upstream (5') of the CD11d gene as shown in FIG. 1. In particular, the invention is directed to cis-acting elements that positively influence the CD11d promoter, increasing the activity of the promoter.

Cis-acting elements that negatively influence the CD11d promoter are also incorporated as part of the present invention. Particularly, the present invention relates to the −591 to −378 region that is upstream (5') of the CD11d gene as shown in FIG. 1 (positions 580 to 793 of SEQ ID NO:1). This cis-acting element contains a cell-specific silencer element.

The invention also relates to the approximately 12 kb sequence that is upstream (5') of the CD11d gene as shown in SEQ ID NO:3. This sequence further comprises additional cis-acting elements which influence the activity of the myeloid cell promoter of the present invention.

Additionally, the invention includes constructs that contain DNA sequences sufficient to direct myeloid cell specific expression of a gene. These constructs comprise both the promoter of the present invention and a heterologous gene, whereby the expression of the heterologous gene is under the control of the myeloid cell specific promoter. The invention is also directed to constructs that contain one or more cis-acting elements of the present invention together with the promoter of the present invention, both linked to a heterologous gene, whereby the expression of the heterologous gene is under the control of the myeloid cell specific promoter of the present invention, and the promoter is influenced by the cis-acting element(s) of the present invention.

The invention also includes cells that have been transfected with a construct of the present invention.

In addition, the present invention relates to methods of producing a selected heterologous gene product in a myeloid cell. These methods include introducing into the myeloid cell a heterologous gene under the control of a myeloid cell specific promoter, or a cis-acting element that influences the activity of the myeloid cell specific promoter, or both. The invention also includes cells produced by the methods described herein.

The present invention also relates to a method for identifying factors that can regulate myeloid cell specific transcription.

Further, the invention relates to a method of expressing a selected heterologous gene product in myeloid cells of an individual, i.e., gene therapy. According to this embodiment, cells produced by the methods described herein are introduced into an individual, wherein they express a heterologous gene under transcriptional control of a myeloid cell specific promoter or a cis-acting element that influences the activity of the cell specific myeloid promoter, or both.

The present invention provides a means of insuring that a selected product, such as a diagnostic, therapeutic or prophylactic substance, is expressed from a specific cell type, in vivo. Therefore, the present invention is useful, for example, for gene therapy or to drive the expression of antiviral agents, such as anti-HIV constructs. The present invention also provides novel promoters which may used to produce cancer vaccines. The present method is also useful in research, for example, to test the effect of the specific expression of heterologous genes, such as oncogenes, in specific cell types. Cells of the present invention are also useful for screening compounds for their effect on myeloid cell specific gene expression.

Further objects, features and advantages of the invention will be apparent from the following detailed description when taken in conjunction with the accompanying drawings.

BRIEF DESCRIPTION OF THE DRAWINGS

FIG. 1 shows the DNA sequence of the CD11d 5'flanking region and exons 1–7 and shows the sequence analysis data for the −946 to +74 CD11d promoter region (positions 225 to 1244 of SEQ ID No: 1). The complete sequence in lowercase for introns 1, 3 and 4, and the sequence at the intron-exon junctions for introns 2, 5, 6 and 7 and their sizes are shown. Consensus gt/ag splice junctions are underlined. Putative binding sites for transcription factors are underlined and indicated above the sequence. The transcriptional start site (+1), the ATG translational start site (boxed), and protein sequence (SEQ ID NO: 2) are shown.

FIG. 9 shows the DNA sequence of the approximately 11.5 kb region located upstream (5') of the region coding for CD11d, CD11d exons and introns 1–7 for CD11d (SEQ ID No: 3).

DETAILED DESCRIPTION OF THE INVENTION

Figure 2:
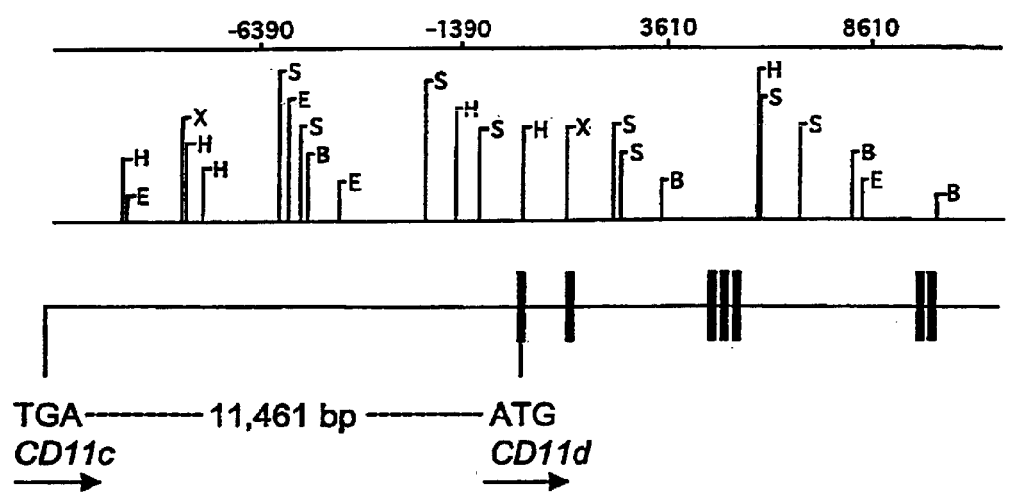
FIG. 2 depicts a CD11d restriction map and location of exons. The location of the translational stop codon (TGA) for CD11d is shown. The direction of transcription of CD11c and CD11d is indicated with arrows. CD11d exons 1–7 are depicted as thickened vertical lines below the location of restriction enzyme sites for EcoRI (E), Hindiii (H), Xbal (X), SacI (S), and BamHI (B). The reference point for the scale in bp is the CD11d transcriptional start site assigned as +1.

The following defined terms are used throughout the application:

Cis-acting element: A term used to describe a component of a DNA sequence which influences the activity of the same or immediately adjacent DNA sequence. For example, the DNA sequences to which transcription factors bind within promoters are said to be cis-acting control elements as they effect the expression of the adjacent gene or gene on the same chromosome.

CD11: A family of four leukocyte-associated single chain molecules that consist of two polypeptide chains; the larger of these chains ($\alpha$) is different for each member of the family and includes CD11a, CD11b, CD11c and CD11d; the smaller chain ($\beta$) is common to all four large chain molecules.

Construct: Recombinant DNA sequences, both linear and circular, that comprise a functional portion of the myeloid cell specific promoter and/or cis-acting element(s) together with DNA encoding a heterologous gene. The myeloid cell specific promoter and/or cis-acting element(s) are functionally linked to the heterologous gene in the constructs described herein.

Functional portion: refers to DNA sequences which are of sufficient size and sequence to have a desired function. In the present application, the desired function is the ability to cause tissue specific expression of a heterologous gene, or the ability to influence the activity of a promoter of the present invention.

Heterologous gene: Genes or DNA sequences which are not normally present in the cell as obtained, or which are not ordinarily functionally associated with a myeloid cell specific promoter region in the cell as obtained, or which are not ordinarily functionally associated with a myeloid cell specific cis-acting element that influences the activity of the cell specific myeloid promoter in the cell as obtained.

Hybridizes: A DNA hybridizes to a second DNA if the first DNA has sufficient nucleic acid sequence complementarily to the second DNA to allow the formation of base pairing and hydrogen bonding under standard DNA hybridization conditions between the two DNAs.

Myeloid cell: Includes monocytes, granulocytes, macrophages, mast cells, erythrocytes, dendritic cells and natural killer (NK) cells, and precursor cells in these cell lineages.

Myeloid cell specific promoter: A DNA sequence which functions as a transcriptional control element or elements and which directs the expression of a gene which is expressed in myeloid cells and which is expressed at reduced efficiency or not at all in other cell types and can include all or a portion of a DNA sequence which functions as a transcriptional control element.

Substantially similar: Two sequences that have a substantial degree of DNA or RNA sequence homology to each other.

The present invention is based on the isolation of a myeloid cell specific promoter and the demonstration that this promoter directs myeloid specific expression of a heterologous gene in transfection assays in vivo, and that the promoter is not capable of directing expression of heterologous genes in cancer cells. The particular myeloid cell specific promoter of the present invention is the CD11d promoter.

The CD11d promoter of the present invention is all or a functional portion of isolated or recombinant SEQ ID NO: 1, such that the sequence is sufficient to direct myeloid cell specific expression of a gene.

It has been surprisingly and unexpectedly discovered that the −946 to +74 region (positions 225 to 1244 of SEQ ID NO:1), as illustrated in FIG. 1, contains the promoter activity for the CD11d gene. More specifically, it has been surprisingly and unexpectedly discovered that the −173 to +74 region (positions 998 to 1244 of SEQ ID NO:1) is sufficient to confer leukocyte-specific expression of a gene in myeloid cells, when the gene is a heterologous gene, such as a luciferase reporter gene.

These sequences which have CD11d promoter activity may further be modified. These modifications may be obtained by mutation, deletion and/or addition of one or more nucleotides in relation to the native sequence. They can be introduced in particular in order to improve the promoter activity, to suppress a transcription inhibiting region, to make a constitutive promoter regulatable or vice versa, to introduce a restriction site facilitating subsequent cloning steps, to eliminate the sequences which are not essential to the transcriptional activity, and the like. Such modifications may be made by any means well known in the art. See., Noti et al., Molec. Cell. Biol. 16:2940–50(1996) and Noti et al., Molec. Immunol. 33:115–127 (1996), for methodologies using PCR to create and/or modify sequences.

The modified sequences may be screened for activity to determine if they retain the CD11d promoter activity. Such screening methodologies are well known in the art, and are further described in the following Examples.

The present invention is further based on the discovery of one or more cis-acting elements present within SEQ ID NO:1 that influence the CD11d promoter activity. Specifically, it has been discovered that several cis-acting elements are present upstream (5') of the CD11d gene that influence the CD11d promoter. This influence may be either to increase or decrease the activity of the myeloid cell specific promoter. The cis-acting element comprises a portion of SEQ ID NO:1 that is sufficient to influence the activity of the myeloid cell specific promoter. In particular, the present invention relates to portions of this sequence that are sufficient to function as a cis-acting element that influences the activity of the myeloid cell specific promoter, and also includes modifications of this sequence that retain sufficient activity to influence the activity of the myeloid cell specific promoter. The modifications would be created and screened in manners similar to those used to identify the promoter modifications as previously described.

Introns are known in the art to often have regulatory sequences contained therein. The invention contained herein also comprises the discovery of introns 1–6 which are shown in FIG. 9 (SEQ ID NO:3). The regulatory sequences contained within these introns can be determined by means well known in the art.

A preferred cis-acting element is the −173 to +74 region that is upstream (5') of the CD11d gene as shown in FIG. 1 (positions positions 998 to 1244 of SEQ ID NO:1). This cis-acting element regulates cell-specific downregulation of CD11d by 4-phorbol-12-myristate 13-actetate (PMA). Also preferred is the −72 to −40 (positions 1099 to 1131 of SEQ ID NO:1), more specifically, the −63 to −40 region (positions 1108 to 1131 of SEQ ID NO:1) that is upstream (5') of the CD11d gene. This cis-acting element binds the transcription factor Sp1. It has been found that purified Sp1 binds at the −63 to −40 (positions 1108 to 1131 of SEQ ID NO:1) region that is upstream (5') of the CD11d gene; whereas crude protein extract that contains Sp1 binds to a larger region, namely, the −72 to −40 (positions 1099 to 1131 of SEQ ID NO:1) region that is upstream (5') of the CD11d gene. It has been discovered that a functional Sp1 binding site is necessary for high levels of CD11d promoter activity. The presence of these cis-acting elements positively influence the CD11d promoter, increasing the activity of the promoter.

It has also been discovered that Sp3 also influences upregulation of the CD11d promoter. Binding of Sp3 occurs in the regions identified in FIG. 9 (SEQ ID NO:3).

Cis-acting elements that negatively influence the CD11d gene are also incorporated as part of the present invention. Most notably, it has been discovered that the −591 to −378 region shown in FIG. 1 (positions 580 to 793 of SEQ ID NO:1) contains a cell-specific silencer element. As described in the following Examples, evidence of a cell-specific silencer element within the −591 to −378 region (positions 580 to 793 of SEQ ID NO:1) that serves to downregulate CD11d expression in Jurkat and IM-9 cells was found.

Additional cell-specific cis-acting elements that lie upstream of −944 of SEQ ID NO:1 are also part of the present invention. These cis-acting sequences lie within the approximately 12.5 kb region described in SEQ ID NO:3. Determination of these cis-acting elements is performed as described in the following Examples, or by any other means well known in the art.

The myeloid cell specific promoter(s) and cis-acting element(s) of the present invention can be obtained from a naturally-occurring source, or they can be produced using any of a variety of techniques, such as genetic engineering or cloning methods, PCR amplification or other synthetic techniques well known in the art.

The CD11d promoter is a strong promoter of expression in myeloid cells. Therefore, in addition to cell specific expression, the CD11d promoter offers the advantage of high level of expression of a desired product in myeloid cells.

Further the invention includes an isolated nucleic acid strand that hybridizes to either a nucleic acid strand having the sequence listed above (SEQ ID NO: 1) or its complement, and constructs containing such isolated nucleic acid strands.

Additionally, the invention includes constructs that contain DNA sequences sufficient to direct myeloid cell specific expression of a gene. These constructs include constructs comprising both the promoter of the present invention and a heterologous gene, whereby the expression of the heterologous gene is under the control of the myeloid cell specific promoter. These constructs are constructed by methods well known in the art, including those exemplified in the following Examples.

Accordingly, the present invention also extends to a construct comprising a DNA sequence having CD11d promoter activity and/or cis-acting element activity according to the invention and a gene of interest placed under its control. It goes without saying that a construct according to the invention may contain several genes of interest either within the framework of a multicistronic construct (schematically represented by the "cis-acting element and/or promoter-gene 1-gene 2 . . . " arrangement) in which the different genes are placed downstream of the cis-acting element and/or the promoter according to the invention and are separated from each other by appropriate sequences, such as the IRES (for Internal Ribosome Entry Site) elements allowing the reinitiation of translation or alternatively within the framework of a bidirectional construct ("gene 1-promoter-gene 2") in which a cis-acting element and/or promoter according to the invention is inserted between two genes of interest in order to control their expression simultaneously.

For the purpose of the present invention, a gene of interest may be derived from a eukaryotic or prokaryotic organism or from a virus. It can be isolated by any conventional molecular biology technique or can be synthesized by the chemical route.

Moreover, a gene of interest may encode a polypeptide of interest corresponding to all or part of a protein as found in nature (native or truncated protein). It may also be a chimeric protein, for example coming from the fusion of polypeptides of diverse origins or from a mutant exhibiting improved and/or modified biological properties. Such a mutant can be obtained by conventional molecular biology techniques. Among the proteins or polypeptides of interest, there may be mentioned by way of nonlimiting examples: cytokines and growth factors.

A construct according to the invention may, in addition, comprise additional elements necessary for the expression of the gene of interest (intron sequence, transcription terminator sequence and the like) or alternatively for its maintenance in the host cell considered. Such elements are known to persons skilled in the art.

The invention also includes cells that have been transfected with a construct of the present invention. The cells are transfected by the constructs of the present invention by any means well known in the art, including electroporation as taught in the following Examples. Other well known methods of transfecting cells with constructs of the present invention include liposome-mediated transfections and $CaPO_4$-mediated transfections.

A host cell to be transfected according to the present invention may be derived from cells which include, but are not limited to, myeloid cells—HL60, THP1 (both macrophage cells), dendritic cells, T cells (Jurkat, RH9 cells), and B cells (IM9, Burkitt Daudi cells).

The present invention further relates to a method of transfecting a myeloid cell line which comprises contacting a suspension of the cells with a heterologous gene construct, and exposing the cells to electroporation. In one embodiment of the invention the heterologous gene construct is a plasmid. In the preferred embodiment, the plasmid is a luciferase vector, such as firefly luciferase driven by the early SV40 enhancer/promoter.

The present invention is based, in part, on the discovery of an efficient technique for transfecting myeloid cell lines, and the discovery that the human genomic region upstream of (5' of) the genomic region encoding CD11d comprises a sequence which contains a control element(s) which is capable of directing myeloid specific transcription of a heterologous gene in transfected myeloid cells. This sequence is also capable of directing reduced, but good, expression of genes within T and B cells, and reduced expression of genes in epithelial cells.

The present invention further includes a method for identifying factors which can regulate myeloid cell specific transcription. This method comprises (a) obtaining a myeloid cell which contains (e.g., has been transfected with, or is derived from a cell transfected with) a heterologous gene under the transcriptional control of a myeloid cell specific promoter (i.e., a myeloid cell promoter-heterologous gene construct); (b) contacting the cell containing the myeloid cell promoter-heterologous gene construct with a selected factor; and (c) assaying for expression of the heterologous gene and comparing its expression in cells contacted with the factor with expression of the gene in cells not contacted with the factor, and thereby determining whether the expression pattern of the heterologous gene is altered in cells contacted with the factor as compared to that of cells which have not been contacted with the factor. The construct and transfected cells are prepared as previously described. The assay is performed as described in the following examples.

Myeloid cell specific promoter-heterologous gene constructs, cis-acting element-heterologous gene constructs, or cis-acting element/myeloid cell specific promoter-heterologous gene constructs can be used to screen for and identify regulators of cell specific transcription. For example, myeloid cells may be transfected with DNA constructs containing functional portions of a myeloid cell specific promoter or cis-acting elements and a heterologous gene in the presence of a variety of potential transcription factors; the ability of the transcription factors to alter the function of the promoter or the cis-acting element may then be tested by assaying for alterations in expression of the heterologous gene.

The promoter(s) and cis-acting element(s) of the present invention may be used in a number of applications. These promoter(s) and cis-acting element(s) provide a means of insuring that a selected product, such as a diagnostic, therapeutic or prophylactic substance, is expressed from a myeloid cell type in vivo. Therefore, the present invention is useful, for example, for gene therapy or to drive the expression of antiviral agents, such as anti-HIV constructs.

The present invention also provides novel promoters which may used in the production of cancer vaccines.

The present method is also useful in research, for example, to test the effect of the specific expression of heterologous genes, such as oncogenes, in specific myeloid cell types.

Cells of the present invention are also useful for screening compounds for their effect on myeloid cell specific gene expression.

This invention is illustrated further by the following nonlimiting Examples. All of the references listed in the application are intended to be incorporated by reference.

EXAMPLE 1

Methodologies and Materials For Identification of CD11d Promoter

The following methodologies and materials were used in the following Examples:
A. Cell Culture The cell lines used were: THP-1 (acute monocytic leukemia, ATCC TIB-202), HL60 (promyelocytic leukemia, ATCC CCL 240), IM-9 (B-cell multiple myeloma, ATCC CCL-159), Jurkat (T-cell acute leukemia, ATCC TIB 152), MCF-7 (breast adenocarcinoma, ATCC HTB-22) and Schneider's *Drosophila* 2 (*D. Melanogaster* embryo, ATCC CRL 1963). THP-1, HL60, and Jurkat cells were grown in RPMI-1640 medium containing 10% fetal calf serum (Biofluids, Rockville, Md.). IM-9 cells were grown in RPMI-1640 medium containing 20% fetal calf serum (Biofluids, Rockville, Md.). HeLa and MCF-7 cells were grown in Dulbecco's modified Eagle's medium containing 10% fetal calf serum (Biofluids, Rockville, Md.). *Drosophila* Schneider 2 cells were grown in Schneider's medium containing 10% insect-tested fetal calf serum (Sigma, St. Louis, Mo.). All media contained 100 U\ml of penicillin and 100 U\ml streptomycin.

B. Plasmids

A series of 5'-unidirectional deletions of the −946 to +74 region (positions 225 to 1244 of SEQ ID No: 1) of the CD11d promoter were prepared by the polymerase chain reaction (PCR) with oligonucleotide primers specific to this region and fused to the firefly luciferase gene (luc) in plasmid pGL3-Basic (Promega Corp., Madison, Wis.). The foreward and reverse primers used in the PCR contained XhoI and HindIII restriction sites, respectively, for cloning of the final PCR product into pGL3-Basic. The −500 to +93 region of the CD11a promoter (positions 671 to 1263 of SEQ ID NO:1), the −500 to +50 region of the CD11b promoter (positions 671 to 1220 of SEQ ID NO:1), and the −196 to +30 region of the CD11c promoter (positions 975 to 1200 of SEQ ID NO:1) were prepared in a similar manner and ligated into pGL3-Basic by the methods of Noti et al. and Noti. Noti, J. D., et al., Mol. Cell. Biol. 16:2940–2950 (1996); Noti, J. D., J. Biol. Chem. 272:24038–24045 (1997).

A primer containing a deletion of the Sp1-binding site (−63 to −40, positions 1108 to 1131 of SEQ ID NO:1) was used in the PCR to construct reporter plasmid CD11d(−173/+74)(−63/−40)-luc. The plasmid pPacSp1, which expresses Sp1 from the *Drosophila* actin promoter, and the control plasmid pPacO, containing only the *Drosophila* actin promoter, were additionally utilized. The construction of plasmids that express Sp2 and Sp3 from the actin promoter (plasmids pPacSp2 and pPacSp3, respectively) were prepared as described by Noti, J. D., J. Biol. Chem. 272:24038–24045 (1997). The integrity of all constructs was verified by DNA sequence analysis.

C. Transfections and Reporter Assays

Transfections of human cells were performed by electroporation as taught by Noti et al., DNA and Cell Biol., 11:123–138 (1992). The transfected cells were analyzed with the Dual-Luciferase Reporter Assay System (Promega Corp., Madison, Wis.). Approximately $1 \times 10^7$ cells of each leukocyte line or $2 \times 10^6$ of MCF-7 cells were co-transfected with 15 μg of each firefly luciferase reporter plasmid and 5 μg of pRL-SV40 Vector (Promega Corp., Madison, Wis.). The pRL-SV40 vector contains *Renilla* luciferase driven by the early SV40 enhancer/promoter. This vector provided an internal control in which to normalize expression from each firefly luciferase reporter. Electroporated cells were transferred to tissue culture dishes containing 15 ml of medium, and, under certain conditions, phorbol 12-myristate 13-acetate (PMA, 10 ng\ml final concentration) was added one hour later. The cells were harvested 24 hr. post-transfection and luciferase activity was assayed. Firefly luciferase light output was measured in a LB96V-2 Wallac Berthold plate luminometer and normalized against *Renilla* luciferase from the co-transfected vector or against the total protein concentration in the cellular extract. DNA was introduced into *Drosophila* cells by calcium phosphate-mediated transfection as taught by Noti et al., Mol. Cell. Biol., 16:2940–2950 (1996). Approximately $3 \times 10^6$ *Drosophila* cells were transfected with 15 μg of a specific luciferase reporter plasmid and 5 μg of pPacSp1, pPacSp2, or pPacSp3. The total volume of the plasmid transfection mix was adjusted to 30 μg with the empty cassette plasmid pPacO. The calcium phosphate-DNA precipitates were left on the cells for 48 hr. prior to harvesting and assaying for luciferase activity. Most transfections were performed in triplicate and repeated two to three times to ensure reproducibility. Statistical analysis was performed using Microsoft Excel (Microsoft Corp, Roselle, Ill.). Data from individual experiments were pooled and expressed as the mean+/−standard deviation (S.D.).

D. In Vitro DNase I Footprinting Analysis

The PCR was performed to prepare a double-stranded probe to the −173 to +74 region (positions 998 to 1244 of SEQ ID NO:1) and one primer was labeled with $[\gamma^{32}P]ATP$. The probe was purified by electrophoresis through a 2% agarose gel on to NA45-DEAE paper according to the manufacturer's instructions (Schleicher and Schuell, Keene, N.H.). Approximately $1-2 \times 10^5$ cpm of probe (1–2 ng), and either 50 μg crude nuclear extract protein (prepared according to Noti et al., DNA and Cell Biol. 11:123–138 (1992)) or 1 to 4 footprinting unit (fpu, concentration determined by the manufacturer) (Promega Corp., Madison, Wis.) of purified Sp1 protein, were incubated in a total volume of 50 μl binding buffer containing 0 or 5 μg poly d(I-C), 6.25 mM $MgCl_2$, 50 mM KCl, 0.5 mM EDTA, 10% glycerol, 0.5 mM DTT, and 25 mM Tris-HCl, pH 8.0, for 15 min. at room temperature. Then 50 μl of 5 mM $CaCl_2\backslash 10$ mM $MgCl_2$, and 0.2–2 units of DNase I were added. After 1 min. at room temperature the reaction was stopped with 90 μl of 0.2 M NaCl, 0.03 M EDTA, 1% SDS, 10 μg *Escherichia coli* tRNA, phenol\chloroform extracted, ethanol precipitated, and analyzed on a sequencing gel.

E. In Vivo Footprinting Analysis

The genomic DNAs from HL60, Jurkat, and IM-9 cells were purified from lysed cells by treatment with proteinase K followed by extensive phenol\chloroform extractions as taught by Mueller et al., In Current Protocols in Molecular Biology (F. A. Ausubel et al., eds.) pp. 15.5.1–15.5.26 (Greene Publishing and Wiley Interscience, NY) (1995). The genomic DNAs were treated either in vivo or in vitro with dimethyl sulfate (DMS), cleaved with piperidine, and analyzed by ligation-mediated PCR as described by Noti et al., Mol. Cell. Biol., 16:2940–2950 (1996) and Mueller et al., In Current Protocols in Molecular Biology (F. A. Ausubel et al., eds.) pp. 15.5.1–15.5.26 (Greene Publishing and Wiley Interscience, NY) (1995). The unidirectional linker was composed of two oligonucleotides, 5' GCGGTGATCCCGGGTGATCTGAAT 7' (SEQ ID NO:3) and 5' ATTCAGATCA 3' (SEQ ID NO8). For footprinting the non-coding strand, the gene-specific primers corresponded to the following regions of the CD11d promoter: prier #1, 5' CTGGGAGAAGGAAGCCAGGTC 3' (SEQ ID NO:9) (for first strand synthesis from the denatured DNAs), which spanned the region −171 to −151 (positions 1000 to 1020 of SEQ ID NO:1); primer #2, 5' CAGGTTGTGGAGGGGGACAGAATGAGG 3' (SEQ ID NO:10) (amplification primer), which spanned the region −146 to −120 (positions 1025 to 1051 of SEQ ID NO:1); and primer #3, 5' GGTTGTGGAGGGGGACAGAATGAGGGTT-TTTCC 3' (SEQ ID NO:11) (labeling primer), which spanned the region −144 to −112 (positions 1027 to 1059 of SEQ ID NO:1). First strand synthesis was done for 30 min. at 60° C. The DNAs were denatured for 4 min. at 95° C. and amplified by the PCR (18 cycles) as follows: 1 min. at 95° C., 2 min. at 68° C., and 3 min. at 76° C. An extra 5 seconds was added to each extension step and the final extension proceeded for 10 min. Two additional cycles of the PCR were carried out to label the PCR products as follows: 1 min. at 95° C., 2 min. at 69° C., and 10 min. at 76° C. An approximately equal amount of each sample was loaded on a sequencing gel. The band intensities were analyzed on a Storm Phosphoimager.

F. RNase Protection, S1 Nuclease Analysis, and Primer Extension Analysis

The −381 to +74 region of CD11d (positions 790 to 1096 of SEQ ID NO:1) was amplified by the PCR and cloned into the XhoI and HindIII sites of pGEM-7Zf(−) (Promega Corp., Madison, Wis.). This clone was linearized with XhoI, and used as template in an in vitro transcription system to prepare a 562 bp RNA probe (Riboprobe, Promega Corp., Madison, Wis.) that spanned this region according to the manufacturer's instructions. The RNA probe was labeled with [α-32P]UTP to a specific activity of $7 \times 10^7$ cpm/μg, loaded on to a 5% polacrylamide/8 M urea gel, and subsequently eluted into buffer containing 0.5 M ammonium acetate/1 mM EDTA/0.2% SDS. Approximately $1-2 \times 10^5$ cpm of probe was annealed to either 20 μg total RNA from HL60 or yeast cells and hybridized in 20 μl of 80% deionized formamide/100 mM sodium citrate pH 6.4/300 mM sodium acetate pH 6.4/1 mM EDTA for 16–18 hr. at 44° C. Following hybridization, the annealed probe/RNA complexes were treated with various concentrations of RNase A/T1 (Ambion, Inc., Austin, Tex.), extracted with proteinase K and phenol/chloroform, and analyzed on a 5% polyacrylamide/8 M urea gel.

For S1 nuclease analysis, a 247 nucleotide single-stranded DNA probe corresponding to the −173 to +74 region of CD11d (positions 998 to 1244 of SEQ ID NO: 1) was prepared by extension of a 22 nucleotide long primer on the luciferase reporter plasmid containing this region. The probe was end-labeled with [α-32P]ATP (probe specific activity of $5.3 \times 10^7$ cpm/μg). Hybridization of the DNA probe, prepared with the Prime-A-Probe Kit (Ambion, Inc., Austin, Tex.), to either 500 ng THP1 poly (A+) RNA or 20 μg yeast total RNA and subsequent digestion with S1 nuclease was performed according to the instructions in the S1-Assay Kit provided by the manufacturer (Ambion Inc, Austin, Tex.). A second antisense DNA probe, 99 nucleotides long with the 5'-end positioned 19 bp upstream of the ATG codon, was chemically synthesized, end-labeled with [α-32P]ATP (probe specific activity of $2.88 \times 10^8$ cpm/μg) and hybridized with HL60 poly (A+) RNA or yeast total RNA.

Primer extension analysis was performed essentially as described by Noti et al., DNA and Cell Biol., 11:123–138 (1992). 2.5 ng of a primer labeled with [γ-32P]ATP (specific activity of $1 \times 10^9$ cpm/μg) was hybridized to either 500 ng of HL60 poly (A+) RNA, 25 μg HL60 total RNA, or 25 μg yeast total RNA in 15 μl of 150 mM KCl/10 mM Tris-Cl, pH 8.3 for 3 hr. at 50° C. Then, 30.5 μl of a solution containing 29 mM Tris-Cl, pH 8.3 at 42° C./14.72 mM MgCl$_2$/8 mM DTT/6.75 mg actinomycin D/0.2 mM each dATP, dTTP, dGTP, dCTP/20 units placental RNase inhibitor/2.5 units MuLV reverse transcriptase was added and incubation continued for 1 hr. at 42° C. The probe/RNA complexes were digested with RNase A/T1 (Ambion, Inc., Austin, Tex.), extracted with phenol/chloroform, and analyzed on a 5% polyacrylamide/8 M urea gel.

EXAMPLE 2

Isolation and Sequence Analysis of The CD11d 5' Flanking Region

The inventors isolated a genomic clone for CD11d that contains the intergenic region between CD11c and CD11d and the 5'-coding portion of CD11d. Utilizing this genomic clone, the regulatory mechanisms for CD11d expression were determined and the clone analyzed in order to locate the CD11d promoter and cis-acting elements. CD11d is positioned no more than 11.5 kb downstream of CD11c.

A collection of CD11c positive cosmid clones was re-screened for the presence of CD11d. One clone was completely sequenced and contains exons 15–30 of CD11c, and exons 1–6 of CD11d. Exon 7 was located separately on another clone. The genes were arranged in the same orientation, with the translational stop codon of CD11c positioned 11,461 bp upstream of the translational start codon of CD11d, as shown in FIG. 2. The sequence of the 1.2 kb 5'-flanking region and exons 1–7 are shown in FIG. 1.

DNA sequence analysis of this clone showed that the ATG translational codon for CD11d lies approximately 11,460 bp downstream of the translational stop codon for CD11c and that both genes are transcribed in the same direction, as shown in FIG. 2.

As illustrated in FIG. 1, the CD11d genomic clone was found to contain exons 1–7 not previously known in the art, which correspond to nucleotides 1–704 of the CD11d coding sequence (positions 1171–1874 of SEQ ID NO:1). Exon 8 and possibly another exon is predicted to lie between nucleotides 704–982 of CD11d (positions 1874–2152 of SEQ ID NO:1), which would be consistent with an average exon size of 100–150 nucleotides.

EXAMPLE 3

Determination of the Transcriptional Start Site of the CD11d Gene

Poly (A+) RNA and total RNA from myeloid HL60 cells was subjected to primer extension analysis with primers N379 (antisense primer with 5'-end positioned 20 nucleotides downstream of the ATG start site) and N470 (antisense primer with 5'-end positioned immediately upstream of the ATG start site), respectively. The longest extension product obtained with N379 was 101 nucleotides long, positioning the transcriptional start site 78 nucleotides upstream of the ATG site. Two extension products, 92, and 93 nucleotides long, were observed with N470 total RNA and would position the transcriptional start site(s) 14 and 15 bp further upstream. No extension products were detected when total yeast RNA was analyzed.

An S1 nuclease protection assay was performed with a 247 nucleotide single-stranded DNA probe that was generated by extension of [γ-32P]ATP-labeled N470 primer on a double-stranded DNA template with exonuclease-free Klenow polymerase. Hybridization of the probe with myeloid THP1 poly (A+) RNA and subsequent S1 nuclease digestion produced four major protected fragments 75–79 nucleotides long and with varying intensities. These results would, therefore, position the start of transcription 75–79 bp upstream of the ATG codon. No protected fragments were produced when the probe was hybridized to yeast total RNA. A second antisense DNA probe, 99 nucleotides long with the 5'-end positioned 19 nucleotides upstream of the ATG codon, was chemically synthesized, end-labeled with [γ-32P]ATP and hybridized with HL60 poly (A+) RNA. S1 nuclease digestion produced four major protected fragments 49–52 nucleotides long, and the most intense fragment was 51 nucleotides long. This second S1 analysis positioned the start of transcription 69 bp upstream of the ATG codon. No protected fragments were produced when the probe was hybridized to yeast total RNA.

An RNase protection assay was performed with a 562 nucleotide long RNA probe prepared by in vitro transcription and uniformly-labeled with [α-$^{32}$P]UTP. The probe included the 455 nucleotides immediately upstream from the ATG codon. Hybridization of the RNA probe with total RNA from HL60 cells and subsequent digestion with RNase A/T1 produced four protected fragments 71–74 nucleotides long. The length of the two most intense fragments would position the transcriptional start site 72 or 74 bp upstream from the ATG codon. No protected fragments were produced when the probe was hybridized to yeast total RNA.

Figure 3:
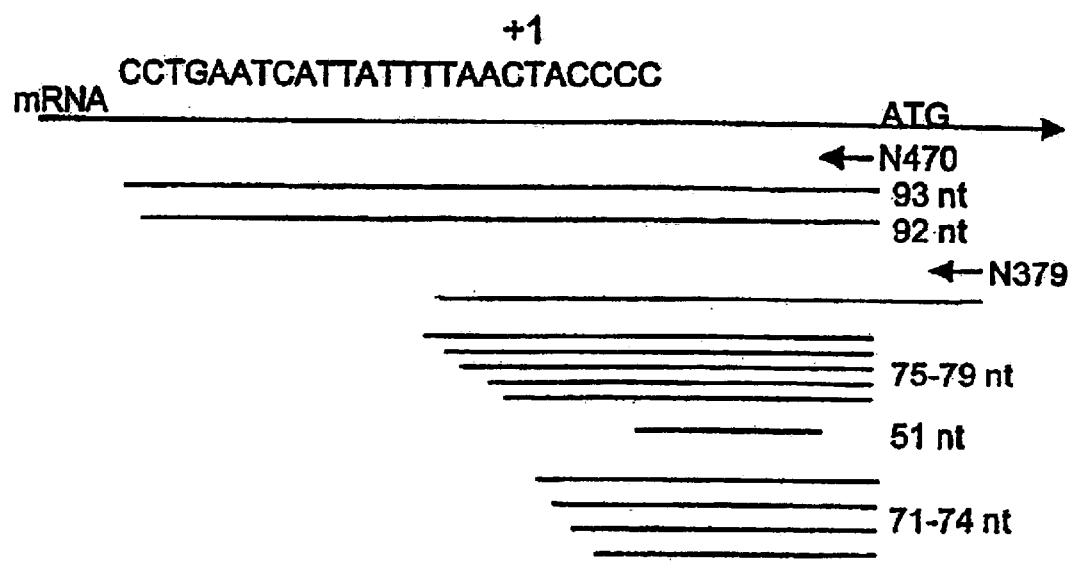
FIG. 3 shows the determination of the transcriptional start site for the CD11d gene with a schematic summarizing the sequencing gel information for the results of the transcriptional assays. (SEQ ID NO: 4 is shown)

Taken together, these results position two transcriptional start sites 69–79 bp and 91–92 bp upstream from the ATG codon. RNase protection assays, which provide for the most stringent hybridization and digestion conditions, and which were repeated five times, consistently confined transcription to within 71–74 bp upstream of the ATG codon. No TATA box is present, and transcription is most probably determined by an initiator (Inr) control element which is found in the CD11a and CD11c genes. Since the 69 to 79 bp region shows homology to the classical Inr, and the largest RNase-protected fragment is 74 nucleotides long, we have assigned the thymidine 74 bp upstream from the ATG codon as the major site (+1) of CD11d transcription. FIG. 3 shows the determination of the transcriptional start site for the CD11d gene with a schematic summarizing the sequencing gel information for the results of the transcriptional assays.

EXAMPLE 4

Functional Analysis of the CD11d Promoter

Figure 4:
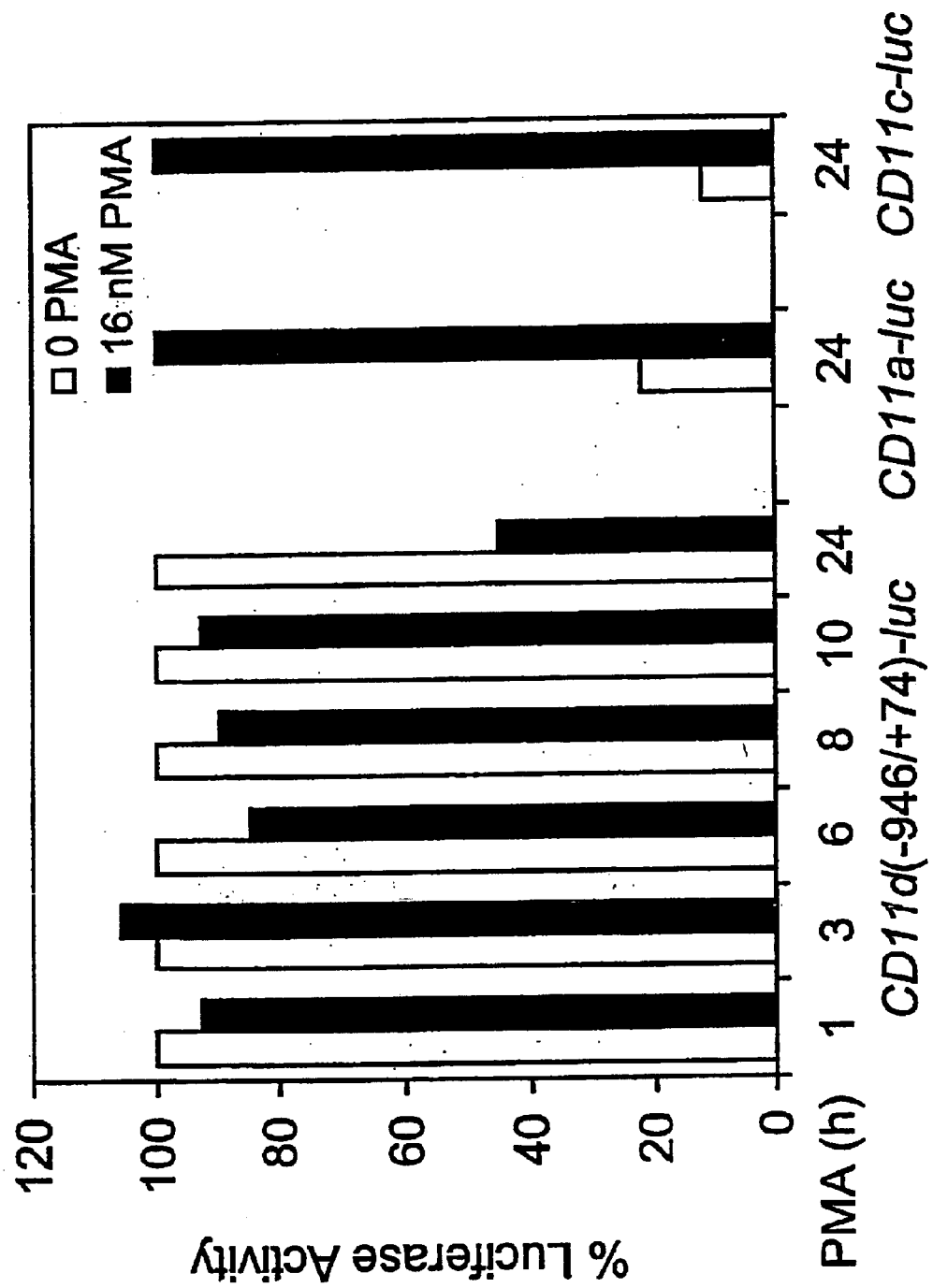
FIG. 4 is a graph illustrating that PMA downregulates the CD11d promoter. CD11d promoter activity in PMA-stimulated cells is expressed relative to that in unstimulated cells after correction for differences in transfection efficiencies.

CD11d is expressed predominately on myeloid cells and exposure to phorbol ester led to its downregulation from the cell surface. THP1 cells were transfected with construct CD11d(−946/+74)-luc, which contains the −946 to +74 region of CD11d (positions 225 to 1244 of SEQ ID NO:1) fused to the luciferase gene, and 24 hr. post-transfection were exposed to PMA for varying times, as shown in FIG. 4. Transfected THP1 cells exposed to PMA for up to 10 hr. showed no decrease in luciferase expression, however, after 24 hr., luciferase activity decreased 55%, as shown in FIG. 4. For comparison, expression of CD11a, which is detected in all leukocytes, and CD11c, which is predominately detected in myeloid cells, were monitored following transfection of the CD11a-luc and CD11c-luc constructs, respectively. Luciferase activity from CD11a-luc in THP1 calls was increased 4.5-fold, and luciferase activity from CD11c-luc was increased 8.3-fold in the presence of PMA, as illustrated in FIG. 4. These results show that chronic, rather than acute, exposure to PMA leads to downregulation of CD11d expression (and upregulation of CD11a and CD11c expression as expected), and that one or more cis-acting elements within the −946 to +74 region (positions 225 to 1244 of SEQ ID NO:1) mediates this effect.

The −946 to +74 region (positions 225 to 1244 of SEQ ID NO:1) was further examined to localize the cis-acting element(s) responsible for PMA-induced downregulation of CD11d and/or other elements that influence either basal or cell-specific expression. A series of CD11d reporter constructs containing progressively larger 5′-deletions was prepared and transfected into various cell lines. Luciferase expression from the constructs transfected into THP1 cells varied, but not significantly.

Figure 5:
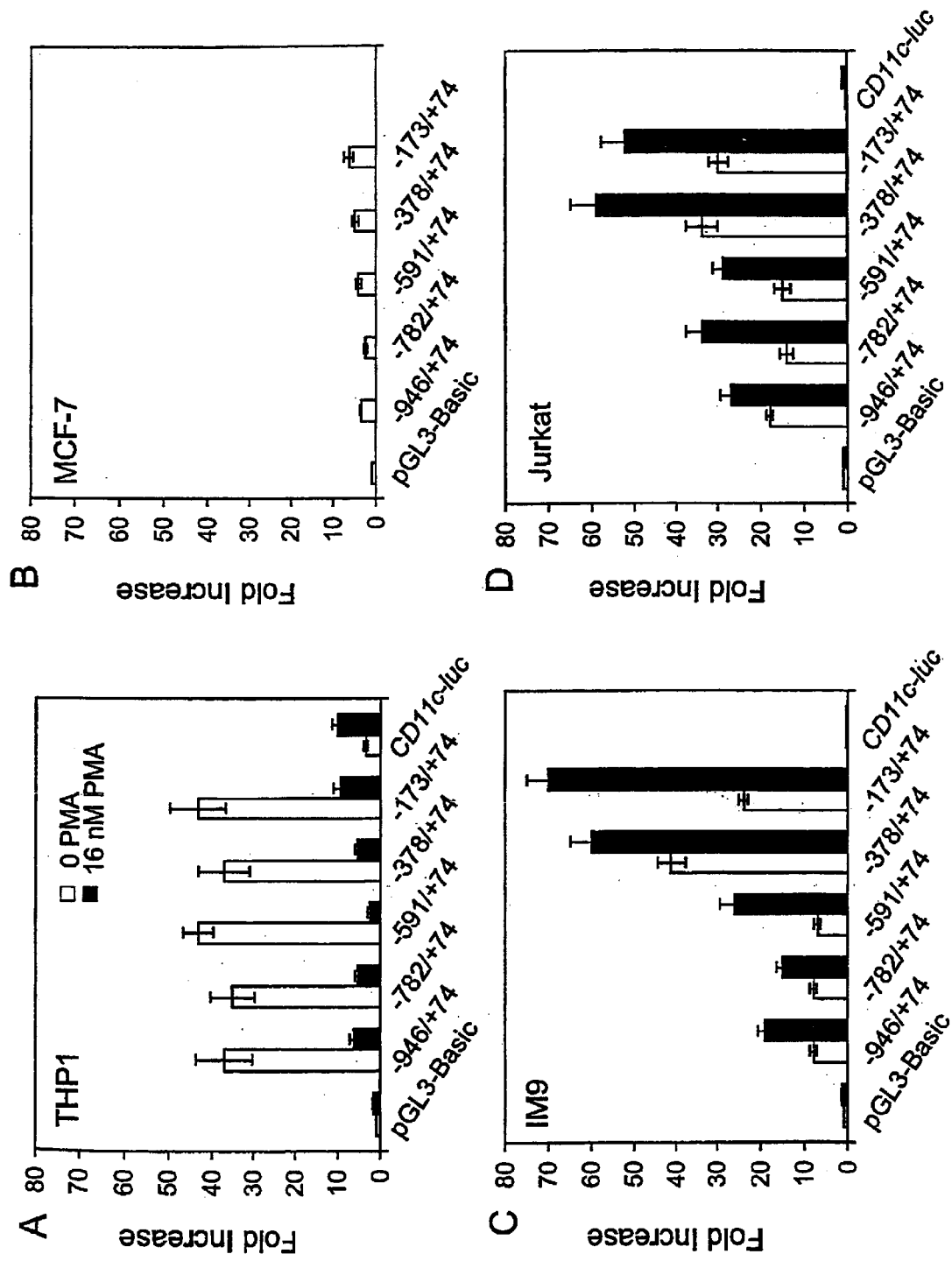
FIG. 5 is a graph illustrating that the effect of PMA on the CD11d promoter is cell specific. The extent of CD11d 5'-flanking sequence in each construct shown is indicated. Promoter activity of each construct is expressed as X-fold increase in activity above the background activity conferred by the promoterless control plasmid pGL3-Basic after correction for differences in transfection efficiencies. Expression of CD11c-luc is shown for comparison. The mean luciferase activities+/−the standard deviations are indicated.

CD11d(−173/+74)-luc, which contains only the −173 to +74 region (positions 998 to 1244 of SEQ ID NO:1) of CD11d, retained all of the activity obtained with CD11d(−946/+74)-luc and was 43-fold higher than that obtained with the promoterless pGL-3 Basic plasmid, as shown in FIG. 5A. In contrast, luciferase expression in MCF-7 breast cancer cells transfected with these constructs was increased only 2.5 to 6.4-fold over that obtained with pGL-3 Basic as shown in FIG. 5B. Expression from CD11d(−946/+74)-luc transfected into the B-cell line IM-9 was also reduced, as luciferase activity was only 8.1-fold over that obtained from pGL3-Basic, as illustrated in FIG. 5C. CD11d(−946/+74)-luc expression in the T-cell line Jurkat, was also reduced, although expression was higher than anticipated as it was 18-fold greater than that obtained from pGL3-Basic, as shown in FIG. 5D. Deletion of the −591 to −378 region (positions 580 to 793 of SEQ ID NO:1) resulted in significant increases in luciferase expression in both IM-9 and Jurkat cells to approximately the level of expression of CD11d(−173/+74)-luc in THP1 cells. See FIGS. 5C and 5D, compare CD11d(−591/+74)-luc with CD11d(−378/+74)-luc. This result indicates the presence of a cell-specific silencer. Luciferase expression from each of the CD11d-luc 5′-deletion constructs transfected into THP1 cells was reduced to approximately the same extent after exposure to PMA, as shown in FIG. 5A. A similar response to PMA was confirmed in another myeloid cell line, HL60, wherein it was discovered that PMA reduces expression in HL60 by 77%. This shows that a PMA-responsive cis-acting element(s) lies within the −173 to +74 region (positions 998 to 1244 of SEQ ID NO:1), since CD11d(−173/+74)-luc, which contains only this region, responds to PMA. In contrast, luciferase expression in IM-9 and Jurkat cells transfected with the CD11d-luc 5′-deletion constructs was not reduced by PMA, but instead, was increased 1.5 to 2.5-fold, see FIGS. 5C and 5D. Together, these results show two regions of CD11d that regulate its expression. The −591 to −378 (positions 580 to 793 of SEQ ID NO:1) region may contain a cell-specific silencer element, and the −173 to +74 region (positions 998 to 1244 of SEQ ID NO:1) regulates cell-specific downregulation of CD11d by PMA.

EXAMPLE 5

Sp1 Binding to CD11d Promoter

DNase I footprint analysis was performed to determine whether DNA binding proteins interact with the −173 to +74 region (positions 998 to 1244 of SEQ ID NO:1). When nuclear extracts prepared from unstimulated and PMA-stimulated THP1 cells were added to a probe labeled on the coding strand, strong protection of the −63 to −40 region (positions 1108 to 1131 of SEQ ID NO:1) was revealed. This same region was also protected by nuclear extracts prepared from unstimulated and PMA-stimulated Jurkat and IM-9 cells. When a probe labeled on the non-coding strand was used, strong protection of an overlapping region, −72 to −45 (positions 1099 to 1126 of SEQ ID NO:1), was detected with unstimulated and PMA-stimulated nuclear extracts from all three cell lines. DNA sequence analysis of the overlapping region revealed the presence of an Sp1 binding site.

In vitro DNase I footprint analysis showed that purified Sp1 protein could also protect the −63 to −40 region positions 1108 to 1131 of SEQ ID NO:1. Electrophoretic mobility shift analysis (EMSA) with THP1 nuclear extract protein and a probe to the −63 to −40 region positions 1108 to 1131 of SEQ ID NO:1 revealed a protein/DNA complex that could be supershifted with anti-Sp1 antibody.

EXAMPLE 6

Sp1 Binding Region Required for CD11d Promoter Activity

To determine whether the Sp1-binding site is important for CD11d expression, this site was deleted from CD11d(−

173/+74)-luc and its effect on expression was monitored in transfected cells. Deletion of the −63 to −40 region (positions 1108 to 1131 of SEQ ID NO:1) resulted in reduction of luciferase expression from CD11d(−173/+74)(−63/−40)-luc to 24% in transfected THP1 cells, as shown in FIG. 6A. When transfected THP1 cells were exposed to PMA, expression from CD11d(−173/+74)-luc was reduced to 30%. Deletion of the −63 to −40 region (positions 1108 to 1131 of SEQ ID NO:1) further reduced luciferase expression from CD11d(−173/+74)(−63/−40)-luc in PMA-stimulated THP1 cells only an additional 7%, as shown in FIG. 6A. Luciferase expression from CD11d(−173/+74)(−63/−40)-luc in transfected IM-9 and Jurkat cells was similarly reduced to 20% and 24%, respectively, as illustrated by FIGS. 6B and 6C. Although PMA did not reduce the expression of luciferase from CD11d(−173/+74)-luc transfected into IM-9 and Jurkat cells, expression from CD11d(−173/+74)(−63/+40)-luc was reduced to 18% and 20%, respectively, as shown in FIGS. 6B and 6C. These results show that the −63 to −40 region (positions 1108 to 1131 of SEQ ID NO:1) is essential for CD11d promoter activity in both myeloid and non-myeloid cells. Further, the inability of PMA to reduce luciferase expression from CD11d(−173/+74)-luc in non-myeloid cells is dependent on the integrity of this region.

EXAMPLE 7

Sp1 Regulation of CD11d

Figure 7:
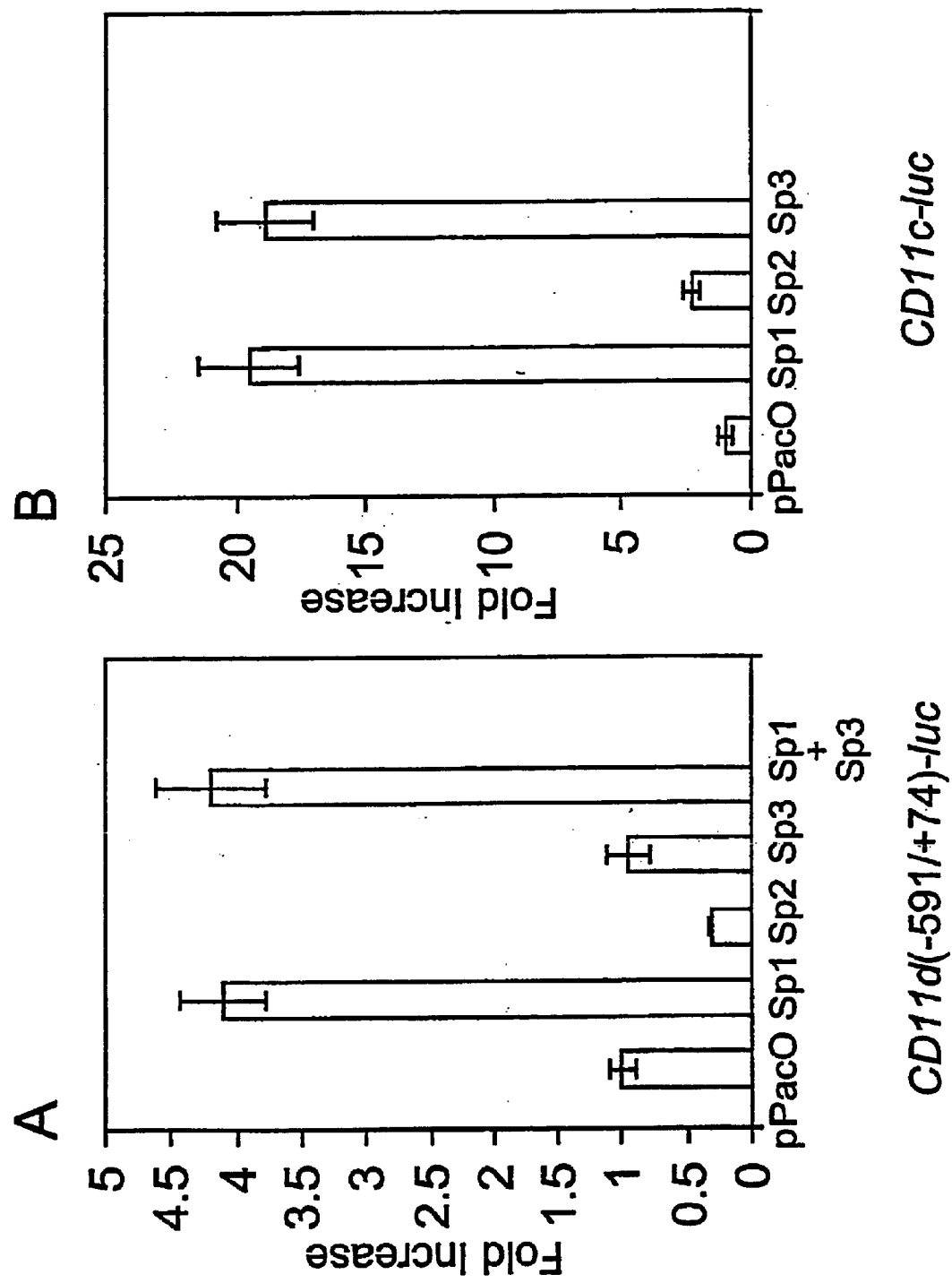
FIG. 7 is a set of graphs showing the induction of the CD11d promoter with Sp1. The mean luciferase activities+/−the standard deviations are indicated.

To show that CD11d promoter activity is mediated through an interaction of Sp1 with the −63 to −40 region (positions 1108 to 1131 of SEQ ID NO:1), *Drosophila* cells, which are deficient in Sp-related proteins, were cotransfected with pPacSp1 along with CD11d(−173/+74)-luc, as shown in FIG. 7.

The role of two other members of the Sp-family, Sp2 and Sp3, expressed from pPacSp2 and pPacSp3, respectively, was similarly analyzed. Sp1-dependent luciferase activity from the CD11d promoter was shown to increase 4.1-fold in *Drosophila* cells cotransfected with pPacSp1 and CD11d(−591/+74)-luc, as shown in FIG. 7A. In contrast, no induction of luciferase activity was seen when either pPacSp2 or pPacSp3 was cotransfected. Analysis of CD11d(−378/+75)-luc in cotransfection experiments yielded similar results.

For comparison, the response of the CD11c promoter to pPacSp1 and pPacSp3 is illustrated in FIG. 7B. As known in the art, CD11c promoter activity is dependent on both Sp1 and Sp3, and was indicated by the 19.5-fold and 18.9-fold induction by Sp1 and Sp3, respectively. It is also known in the art that Sp1 and Sp3 compete for the same sites on the CD11c promoter, however, luciferase activity from CD11d(−591/+74)-luc is maximal in the presence of pPacSp1 alone, and was not further increased when both pPacSp1 and pPacSp3 were present, as shown in FIG. 7A. Since pPacSp1-dependent expression of luciferase from CD11d(−591/+74)-luc is also not decreased in the presence of pPacSp3, Sp3 does not compete with Sp1 for binding to the same site. This suggests that Sp3 does not function as a repressor of CD11d promoter activity, in contrast to its reported repressor-like activity on other promoters.

EXAMPLE 8

Myeloid-Specific Downregulation of CD11d by PMA

Figure 6:
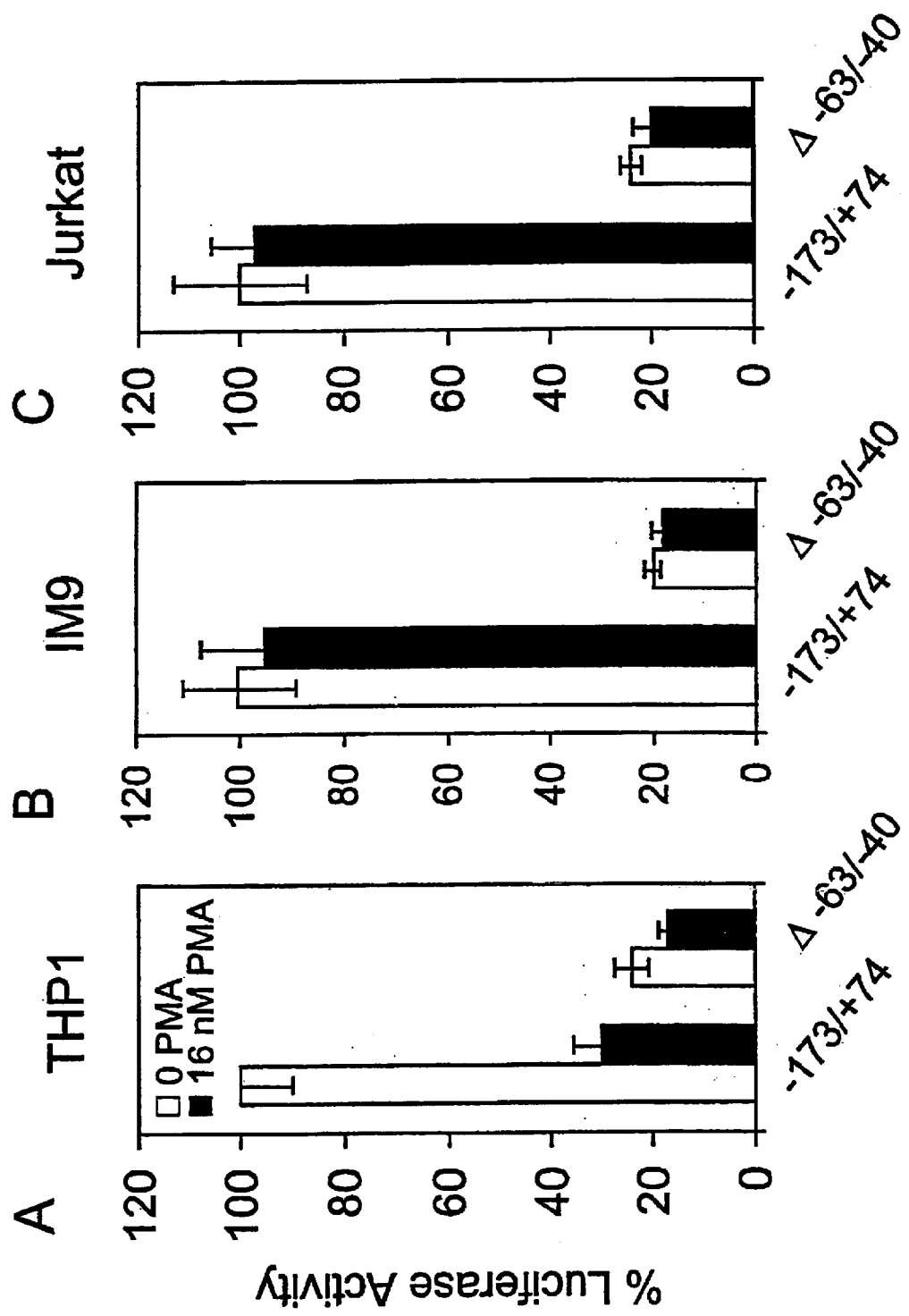
FIG. 6 is a set of graphs illustrating that the Sp1-binding site is essential for CD11d promoter activity. The mean luciferase activities+/−the standard deviations are indicated.

The above results show that cell-specific downregulation of CD11d promoter activity is mediated through one or more cis elements within the −173 to +74 region (positions 998 to 1244 of SEQ ID NO:1). The inability of IM-9 and Jurkat cells to maintain CD11d expression in the presence of PMA when the Sp1-binding site was deleted indicated that Sp1 was a necessary factor involved in this response. Further, the possibility that loss of Sp1-binding was linked to downregulation of CD11d promoter activity in THP1 cells exposed to PMA was suggested when the reduction in luciferase activity from CD11d(−173/+74)-luc in transfected THP1 cells exposed to PMA was found to be about the same as that obtained in unstimulated THP1 cells transfected with the Sp1-deleted construct CD11d(−173/+74)(−63/−40)-luc (70% vs. 76% reduction, respectively, as shown in FIG. 6.

Figure 8:
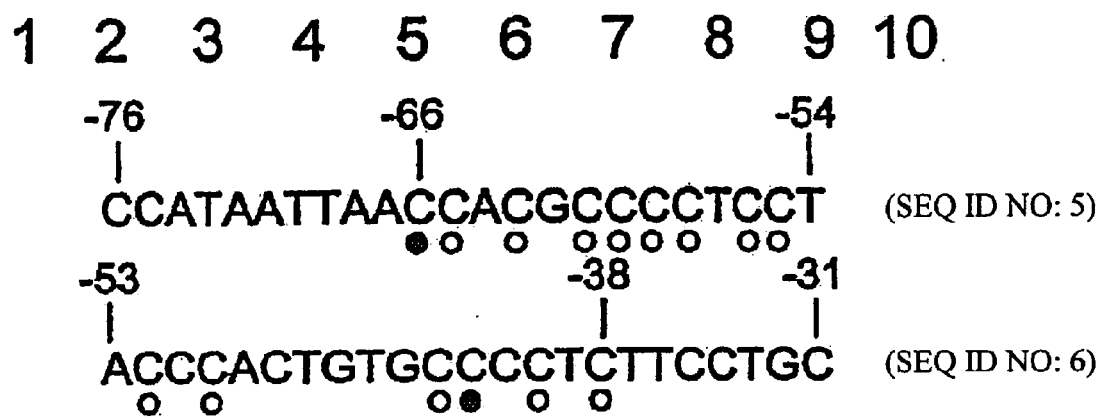
FIG. 8 is a sequence schematic summarizing the results of gel analysis illustrating the loss of Sp1-binding in vivo in PMA-stimulated myeloid cells. The open and gray circles below the sequence refer to the guanidine residues on the non-coding strand. (SEQ ID NO:5 and 6 are shown.)

In vivo genomic footprinting was performed to determine if selective Sp1-binding occurs on the CD11d promoter. Genomic DNA, methylated in vivo with dimethyl sulfate, was isolated from HL60, IM-9, and Jurkat cells that were either unstimulated or PMA-stimulated. DNA was also isolated from HL60 and Jurkat cells, stripped of bound protein, and methylated in vitro as controls. Analysis of the CD11d non-coding strand, as shown in FIG. 8, revealed hyposensitive sites in unstimulated HL60 DNA at positions −38, −40, −42, −43, −50, −52, −55, −56, −58 to −61, −63, −65, and −66 (positions 16, 14, 12, 11, 4 and 2 of SEQ ID NO:6 and positions 22, 21, 19 to 16, 14, 12 and 11 of SEQ ID NO:5, respectively) which correspond to guanine nucleotides in the Sp1-binding site. No protection was seen over these positions on genomic DNA from PMA-stimulated HL60 cells. In contrast, genomic DNAs from IM-9 and Jurkat cells, either unstimulated or PMA-stimulated, were similarly protected over these positions. From these results, we conclude that occupation of the CD11d promoter by Sp1 is significantly reduced in PMA-stimulated myeloid cells, and that myeloid-specific downregulation of CD11d expression is mediated through preferential loss of Sp1 binding following PMA stimulation.

It is understood that the invention is not confined to the particular embodiments set forth herein as illustrative, but embraces all such modified forms thereof as come within the scope of the following claims.

What is claimed is:

1. A promoter of the CD11d gene comprising all or a functional portion of isolated or recombinant SEQ ID NO: 1, wherein the functional portion is selected from the group consisting of 225 to 1244 of SEQ ID NO: 1, and 998 to 1244 of SEQ ID NO: 1.

2. A promoter of the CD11d gene comprising an isolated or recombinant double-stranded DNA molecule, wherein one of the strands of the DNA hybridizes to all or a functional portion of SEQ ID NO: 1, wherein the functional portion is selected from the group consisting of 225 to 1244 of SEQ ID NO: 1, and 998 to 1244 of SEQ ID NO: 1.

3. A cis-acting element that influences the activity of a myeloid cell promoter comprising a functional portion of isolated or recombinant SEQ ID NO: 1, such that the element is sufficient to influence the activity of a myeloid cell specific promoter wherein the cis-acting element is the 225 to 1244 region of SEQ ID NO: 1.

4. A cis-acting element that influences the activity of a myeloid cell promoter comprising a functional portion of isolated or recombinant SEQ ID NO: 1, such that the element is sufficient to influence the activity of a myeloid cell specific promoter wherein the cis-acting element is the 999 to 1244 region of SEQ ID NO: 1.

5. A cis-acting element that influences the activity of a myeloid cell promoter comprising a functional portion of isolated or recombinant SEQ ID NO: 1, such that the element is sufficient to influence the activity of a myeloid cell specific promoter wherein the cis-acting element is the 1099 to 1131 region of SEQ ID NO: 1.

6. A cis-acting element that influences the activity of a myeloid cell specific promoter comprising a functional portion of isolated or recombinant SEQ ID NO: 1, such that the element is sufficient to influence the activity of a myeloid cell specific promoter wherein the cis-acting element is a binding site for a transcription factor, further wherein the cis-acting element is a binding site for Sp1, further wherein the binding site for Sp1 is the 1108 to 1131 (5') region of SEQ ID NO: 1.

7. A cis-acting element that influences the activity of a myeloid cell specific promoter comprising a functional portion of isolated or recombinant SEQ ID NO: 1, such that the element is sufficient to influence the activity of a myeloid cell specific promoter wherein the cis-acting element is a myeloid cell specific silencer element, further wherein the cis-acting element is the 580 to 793 region of SEQ ID NO: 1.

* * * * *

SEQUENCE LISTING

<160> NUMBER OF SEQ ID NOS: 11

<210> SEQ ID NO 1
<211> LENGTH: 3297
<212> TYPE: DNA
<213> ORGANISM: Homo sapiens

```
<220> FEATURE:
<221> NAME/KEY: misc_feature
<222> LOCATION: (1641)..(1645)
<223> OTHER INFORMATION: n can be a, c, g, or t
<221> NAME/KEY: CDS
<222> LOCATION: (1245)..(1275)
<221> NAME/KEY: CDS
<222> LOCATION: (2123)..(2228)
<221> NAME/KEY: CDS
<222> LOCATION: (2308)..(2411)
<221> NAME/KEY: CDS
<222> LOCATION: (2545)..(2615)
<221> NAME/KEY: CDS
<222> LOCATION: (2744)..(2858)
<221> NAME/KEY: CDS
<222> LOCATION: (2936)..(3066)
<221> NAME/KEY: CDS
<222> LOCATION: (3132)..(3275)

<400> SEQUENCE: 1
tttaatcatg gaatatttca aacatacaga aaaatcacag aaaataaata acaaccactc      60
atttatcttc tccccaaccc catgtaataa atattaaaat attgtgttaa atgctaaatt     120
taacacatgc taaaggttcc tggctggatg tggtggctca cgcctgtaat cccagtactt     180
tgggaggagg aggtgggagg attgcttgag tccaggagct cgagaccagc atgggcaaca     240
tagtgcgatc tcgtctctac aaaaaacaaa aaattagct gggcatggtg gtgtgcatca      300
gtaatcccag tgactgggag gctgaggtgg gagaattgct tgagtctggg aatttgaggc     360
tgcagtgagc cctgatcatg ccactgcatt ccagcatggg cgacatagca aaacttgtca     420
aaaaaaaaaa aagtttcctc tctgccccac catagacaac cactcttctg atttctatct     480
tcgtagatga atttttgccca ttctcttgta tatgaaagga accagacatt aggcattctg     540
gtgtctggtt tctttcactt aagataaaat tgagttaacc tgtattgttg tacagaactg     600
cagtttgttc tttgttattt attgtaaaga cagggtctgg ctatgttgcc taggctggtc     660
tcgaactgtt ggcctcaagc aatccacctg ccaagctctg ggaccacagg catgagccat     720
ggcatctgat ckgtagtttg atcttatttc ttgctgagta gtagcccatg gcatgacttt     780
attattttgg gtgtccattc tcctctggag gggctctgct ttttgaaacc acaccctggc     840
ctagctcccc ttctccctgc ctctctgcag gctcacatcc acatgccaag acctctgcag     900
ccattctgct tcctgtcctt ccactcctgt gggacctcag agagctacgg ggctccctgg     960
gtaccaactg gctcctgagg cctgggggag ggtggtcttc tgggagaagg aagccaggtc    1020
cctgcaggtt gtggaggggg acagaatgag ggttttttccc caggatgttg ttggcccctg    1080
cccccacttc tgttccataa ttaaccacgc ccctcctacc cactgtgccc ctcttcctgc    1140
tgtgtggagg ccctgaatca ttattttaac taccccctgg gagggtgagc accttctgtg    1200
ctctgtcccc aaccttccac ttcccctcaa cgcgctgctc aggg atg acc ttc ggc     1256
                                                  Met Thr Phe Gly
                                                  1 act gtg ctt ctt ctg agt g gtaagtgggg ccagggtgct ggggagaagc            1305
Thr Val Leu Leu Leu Ser
  5              10 ttggaggagt tctgagggga ctccatctgg gagggcaggc tggggctgg tggtcggctc      1365 caaccactct tatgaggagc tgaggcaggg gagtgcttca tgtgcgagtg gcccggagtc    1425
agtagagtgt gacctgaatg aagagggget caggggetgt getcaggtgg cgactaagct    1485 acctctccag ctggctatgt tgtcccaggc ttccctgctc ccactcatgg agtccctggt    1545
gtgggtgaca gaggtctccc cagcctcccc cgggagtgga aggccacaga agccaccagg    1605
```

-continued

```
gaggggga aa ggttggacat cacctccctg ggcctnnnnn ttcccccaag tcctgactgc       1665
acgtagggaa gaggcccct gctgaaaact gcatcagagt cacattcacg tgccatcaaa         1725
aatcaggctt ggctgggtgc ggtggctcat gcttataatc ccagcacttt gggaggccga       1785
gatgggcgta tccctgagg tcaggagttt gtgaccagcc tggccaacat ggtgaaaccc         1845
catctttacc aaaatataa aaattagccg ggcatggtgg cgtgcacttg taatcccagc         1905
tacttgggaa gctgaggcaa gagaatcgct tgaacccagg agacggaagt tgcagtgagc       1965
tgagatcgtg ccgttgcact ccagcctcag caacagagcg agactccatc tcaaaaaaaa       2025
aaaaaaaaaa aagaaaaaaa agaaaagag gctgggaggt cctagggatt ggggcttctt         2085
```

```
taactcccag cctccccgcc caccaaatat tcctcag tc  ctg gct tct tat cat       2139
                                            Val Leu Ala Ser Tyr His
                                                              15 gga ttc aac ctg gat gtg gag gag cct acg atc ttc cag gag gat gca         2187
Gly Phe Asn Leu Asp Val Glu Glu Pro Thr Ile Phe Gln Glu Asp Ala
        20                  25                  30 ggc ggc ttt ggg cag agc gtg gtg cag ttc ggt gga tct cg                  2228
Gly Gly Phe Gly Gln Ser Val Val Gln Phe Gly Gly Ser Arg
    35                  40                  45
```

```
gtaggcccca ctcccccaag tgcccgctgc tcccacccct cctgtggctg cagtgacatg       2288
gccatggttg tgtctccag a ctc gtg gtg gga gca ccc ctg gag gtg gtg          2338
                      Leu Val Val Gly Ala Pro Leu Glu Val Val
                                        50                  55 gcg gcc aac cag acg gga cgg ctg tat gac tgc gca gct gcc acc ggc         2386
Ala Ala Asn Gln Thr Gly Arg Leu Tyr Asp Cys Ala Ala Ala Thr Gly
            60                  65                  70 atg tgc cag ccc atc ccg ctg cac a gtgagtgacc acctgggaat                 2431
Met Cys Gln Pro Ile Pro Leu His
    75                  80 tgggcccctc aaccctcctg gacccaactg tgccccgct tagcttccag tccagacctt        2491
ccccgcaaat gagtgtgtgc tgtgagtgag accccgcgtg tctgcccttg cag tc            2546
                                                               Ile cgc cct gag gcc gtg aac atg tcc ttg ggc ctg acc ctg gca gcc tcc         2594
Arg Pro Glu Ala Val Asn Met Ser Leu Gly Leu Thr Leu Ala Ala Ser
            85                  90                  95 acc aac ggc tcc cgg ctc ctg gtgagtgagt gtcttgggcc acgggggggt            2645
Thr Asn Gly Ser Arg Leu Leu
        100 ggggtggggc gggggtgtt gttggggagg aggctgggc tgggagtgaa ggaggagggg         2705 ctgctaggga ctcctggctc acaggcttct gcctccag gcc tgt ggc ccg acc ctg       2761
                                          Ala Cys Gly Pro Thr Leu
                                                              105                 110 cac aga gtc tgt ggg gag aac tca tac tca aag ggt tcc tgc ctc ctg         2809
His Arg Val Cys Gly Glu Asn Ser Tyr Ser Lys Gly Ser Cys Leu Leu
            115                 120                 125 ctg ggc tcg cgc tgg gag atc atc cag aca gtc ccc gac gcc acg cca g       2858
Leu Gly Ser Arg Trp Glu Ile Ile Gln Thr Val Pro Asp Ala Thr Pro
            130                 135                 140 gtaggtccct gcaggagct gcaggagggg gttgggcccc cgcagtgcat ctccgattcc        2918
tccccattcc cccacag ag  tgt cca cat caa gag atg gac atc gtc ttc          2967
                     Glu Cys Pro His Gln Glu Met Asp Ile Val Phe
                                          145                 150 ctg att gac ggc tct gga agc att gac caa aat gac ttt aac cag atg         3015
Leu Ile Asp Gly Ser Gly Ser Ile Asp Gln Asn Asp Phe Asn Gln Met
    155                 160                 165 aag ggc ttt gtc caa gct gtc atg ggc cag ttt gag ggc act gac acc         3063
Lys Gly Phe Val Gln Ala Val Met Gly Gln Phe Glu Gly Thr Asp Thr
```

-continued

```
                170                 175                 180                 185
ctg gtgaagactg ggcaaacaat agtaacaggc actgagccct gggccctccc              3116
Leu cactggcctt tgcag ttt gca ctg atg cag tac tca aac ctc ctg aag atc        3167
                Phe Ala Leu Met Gln Tyr Ser Asn Leu Leu Lys Ile
                                190                 195 cac ttc acc ttc acc caa ttc cgg acc agc ccg agc cag cag agc ctg         3215
His Phe Thr Phe Thr Gln Phe Arg Thr Ser Pro Ser Gln Gln Ser Leu
    200                 205                 210 gtg gat ccc atc gtc caa ctg aaa ggc ctg acg ttc acg gcc acg ggc         3263
Val Asp Pro Ile Val Gln Leu Lys Gly Leu Thr Phe Thr Ala Thr Gly
215                 220                 225                 230 atc ctg aca gtg gtgtaaagca accccgaccc ca                                3297
Ile Leu Thr Val <210> SEQ ID NO 2
<211> LENGTH: 234
<212> TYPE: PRT
<213> ORGANISM: Homo sapiens
<220> FEATURE:
<221> NAME/KEY: misc_feature
<222> LOCATION: (1641)..(1645)
<223> OTHER INFORMATION: n can be a, c, g, or t

<400> SEQUENCE: 2

Met Thr Phe Gly Thr Val Leu Leu Leu Ser Val Leu Ala Ser Tyr His
1               5                   10                  15

Gly Phe Asn Leu Asp Val Glu Glu Pro Thr Ile Phe Gln Glu Asp Ala
                20                  25                  30

Gly Gly Phe Gly Gln Ser Val Val Gln Phe Gly Gly Ser Arg Leu Val
            35                  40                  45

Val Gly Ala Pro Leu Glu Val Val Ala Ala Asn Gln Thr Gly Arg Leu
        50                  55                  60

Tyr Asp Cys Ala Ala Ala Thr Gly Met Cys Gln Pro Ile Pro Leu His
65                  70                  75                  80

Ile Arg Pro Glu Ala Val Asn Met Ser Leu Gly Leu Thr Leu Ala Ala
                85                  90                  95

Ser Thr Asn Gly Ser Arg Leu Leu Ala Cys Gly Pro Thr Leu His Arg
            100                 105                 110

Val Cys Gly Glu Asn Ser Tyr Ser Lys Gly Ser Cys Leu Leu Leu Gly
        115                 120                 125

Ser Arg Trp Glu Ile Ile Gln Thr Val Pro Asp Ala Thr Pro Glu Cys
    130                 135                 140

Pro His Gln Glu Met Asp Ile Val Phe Leu Ile Asp Gly Ser Gly Ser
145                 150                 155                 160

Ile Asp Gln Asn Asp Phe Asn Gln Met Lys Gly Phe Val Gln Ala Val
                165                 170                 175

Met Gly Gln Phe Glu Gly Thr Asp Thr Leu Phe Ala Leu Met Gln Tyr
            180                 185                 190

Ser Asn Leu Leu Lys Ile His Phe Thr Phe Thr Gln Phe Arg Thr Ser
        195                 200                 205

Pro Ser Gln Gln Ser Leu Val Asp Pro Ile Val Gln Leu Lys Gly Leu
    210                 215                 220

Thr Phe Thr Ala Thr Gly Ile Leu Thr Val
225                 230

<210> SEQ ID NO 3
```

<211> LENGTH: 21777
<212> TYPE: DNA
<213> ORGANISM: Homo sapiens
<220> FEATURE:
<221> NAME/KEY: misc_feature
<222> LOCATION: (1641)..(1645)
<223> OTHER INFORMATION: n can be a, c, g, or t
<221> NAME/KEY: misc_feature
<222> LOCATION: (11131)..()
<223> OTHER INFORMATION: n can be a, c, g, or t

<400> SEQUENCE: 3

```
tgatccctct tgccttgga cttcttctcc cgcgattttc cccacttact taccctcacc      60
tgtcaggctg acggggagga accactgcac caccgagaga ggctgggatg ggcctgcttc     120
ctgtctttgg gagaaaacgt cttgcttggg aaggggcctt tgtcttgtca aggttccaac     180
tggaaaccct taggacaggg tccctgctgt gttccccaaa aggacttgac ttcgaatttc     240
tacctagaaa tacatggaca ataccccag gcctcagtct cccttctccc atgaggcacg      300
aatgatcttt cttccttc cttttttttt ttttctttt cttttttttt tttttgaga       360
cggagtctcg ctctgtcacc caggctggag tgcaatggcg tgatctcggc tcgctgcaac     420
ctccgcctcc cgggttcaag taattctgct gtctcagcct cctgcgtagc tgggactaca     480
ggcacacgcc acctcgcccg gcccgatctt tctaaaatac agttctgaat atgctgctca     540
tccccacctg tcttcaacag ctccccatta ccctcaggac aatgtctgaa ctctccagct     600
tcgcgtgaga agtcccctc catcccagag ggtgggcttc agggcgcaca gcatgagagc      660
ctctgtgccc ccatcaccct cgtttccagt gaattagtgt catgtcagca tcagctcagg     720
gcttcatcgt ggggctctca gttccgattc cccaggctga attgggagtg agatgcctgc     780
atgctgggtt ctgcacagct ggcctcccgc ggttgggtca acattgctgg cctggaaggg     840
aggagcgccc tctagggagg gacatggccc cggtgcggct gcagctcacc agccccaggg    900
gcagaagaga cccaaccact tcctattttt tgaggctatg aatatagtac ctgaaaaaat     960
gccaagcact agattatttt tttaaaaagc gtactttaaa tgtttgtgtt aatacacatt    1020
aaaacatgca caaaaagatg catctaccgc tcttgggaaa tatgtcaaag ggtctaaaaa    1080
taaaaaagcc ttctgtggat atgagtcctg aaggatgaca cccatggggt cccttttacca   1140
cggtggaccc tggccagcac tgaggcctgg ggccaggaca agaagttaac cagagtaggg    1200
ttgtgaatat ccctctcttg gaagtaaccct gacctcttaa tctgctcact ccactctcag   1260
ggctggtgcc gatggtaagc tggtggagct gtcgggtgga gggggcatag aatagagaag    1320
ggacaacctc cagtggctac ttttccacct ggaaaggtct ctggagtgac caatactcac    1380
aagcgttccc tacaagtcct aggatgtgtt gaagggcaca ctgtctgcat atagtgagtg    1440
attgaagaac atgttggggt cccacattga gagctgctgc ccacaataag gtcattcttg    1500
ctattatgcc accatcctgg cataaagttc atcatggtgc ttggcactga gctgggggcc    1560
tcacaggaca agccattcct gacctcggag tgacgccact gcagctatca ccagcaaggg    1620
acccgggccg tgtggatgtt tcaattagaa aaacagaagg gaggcagttg agtgatttga    1680
agggaagatg gaaagtggcc ctttacctcc agccaaaaat gtctgtccta tacatcagca    1740
gaggctccaa aatccctgtg gattttgaag cttttgagtc cccaggatga ctaattatta    1800
tgcagtttcc tcagaaaggg aatcagaaga taaggctttg taagaattca gccctaatgg    1860
ctgggcacag tggctcatgc ctgtaatccc agcactttgg gaggccgagg caggaggatt    1920
gtttgtgctc agaaatttga gaccaccctg ggtaatatat tgaaaccttg tgtctacaaa    1980
```

-continued

| | |
|---|---|
| aaaatttaaa aattacccag gcatggtggc atgtgcttgt agtcccagct acttggtagg | 2040 |
| ctgaagcagg aggatcactt gagcctggga ggttgaggat acagtgagct gtgatttgga | 2100 |
| ccaccacact ccagcctggg caacagagaa agatcatgtc tcagaaaaaa aaaaaaaat | 2160 |
| tgaccctaga gtggtgtttc tcaaaatgtg ttccacgaac cactggtggt caatgatggt | 2220 |
| cttctaagtg gaaggtttta gagaaaaaga gcaagaaacc catacatctc aaacatttga | 2280 |
| aactagtgat ttgcacagaa atagtgttgt ggccttaata attgtgtggc acacggactc | 2340 |
| cagggactac agtgggttct tgtctaaatt caggcaacaa gttgttattt tctattttat | 2400 |
| tttattatta ttatttttg agatagtctc actttgtctc ccgggctgga gtgtagtggc | 2460 |
| acgatctcgg ctcaacgcaa cctctgtctc ctgggttcaa gtgatgcctc tgcctcagcc | 2520 |
| tcccaagtag ctgggagtac aggggcgtac caccatgccc attttatttt atttattttt | 2580 |
| gagacagagt ctcgctctgt cacccaggct ggagtgcagt ggcatgatct tggctcactg | 2640 |
| caacctccgc ctcccaggtt caagttcaag cgattctcct gcctcagcct ctggagtagc | 2700 |
| tgggattaca ggcaggcacc accatttcca gctaattttt gtattttag tatagatggg | 2760 |
| gtttcaccat gttgactagg ctggtctcga actcctgacc tcatgatccg ccctcctcgg | 2820 |
| cctccgaaag tgctgggatt agaggtatga gccactgtac ttggccgaca aggtgttatt | 2880 |
| ttctgatatt cttcctttgt gtgttattgt gtacatttgt tacatttgca ttttcagggt | 2940 |
| tggctattgt gttgcattag atccccgaat cacaaaatgg atcaatggct caaaagcatg | 3000 |
| gaagttgtga ttaaaaacta atctaattgc tacaatttac aataatgtca tcaaagtcaa | 3060 |
| tattgacttt taaatattga gcccagtgca cgtatagtat agacatgcat accggaataa | 3120 |
| gtgattgtga gccaaaaccc gaaaatatct agaaggtatt atactccctg acaggtaggt | 3180 |
| tgtattggtt ctgacatgta tttgtcccta gtgtgctgcc cattctgaaa ctttatcaaa | 3240 |
| cagtcgcatg aacctctgaa agcttttgtg ttattttctt atttatttat ttattgagat | 3300 |
| ggagtcttgc tctgtcgccc aggctggagt gcagtggcat catcttggct cactgcaacc | 3360 |
| tttgcctcct gggttcaagt gattctcctg cctcagcctc ttgagtagct gggattacag | 3420 |
| gcgcgcacca ccacgcccag ctaattttg tattttagt atagacgggg gtttcaccat | 3480 |
| gttggtcagg ctggtctcga acccctgacc tcatgatctg cctgcctcag gtaaagcaat | 3540 |
| agagattctt agaacaactg ctacatgtag ctttcctatt caaaagtgat tagtgttgtc | 3600 |
| accgaataca gaggagacag caaaaccaca gtgacataaa tcaaaggtgc ttttaaagt | 3660 |
| agcaaaagta ggtacaagtc acataatttc caagaagctt gtagaaatgg cagtagagtt | 3720 |
| catacctgct attgaaaggt tgcttttggc tgcaaataat agaaaaaaac aaaagcatgt | 3780 |
| aagagcagac agaagacctt tactctgcaa gaggttcagg tgcaggttag tgtttaatgc | 3840 |
| agagtctcag cattgacaga ttcttttctga tcttccaatt gatcgtcctt gcggggggcgg | 3900 |
| tttagttctt tcccactgac taggattggg tcaaattcca tccccttggt tgcatgcagt | 3960 |
| gctgagaagg tgagcatgtg cttttcacag gcttaataaa agaggtagc tccagccagg | 4020 |
| tgcagtgact catgcctata atctcagcac tttgggaggc agaggtgggt aggtcacctg | 4080 |
| aggtcaggag attgagaacc agcctgacca acatggcaaa actctgtctc taccgaaaat | 4140 |
| acaaaaatta gctgggcatg gtggcaggtg cctgtaatcc cagctacttg ggaggctgag | 4200 |
| gcaggagaat cgcttgaacc tgagaggtgg aagttacagt gagctgaggt catgccactt | 4260 |
| gcactccagc ctgggggaca gagtagaact ctgtctcaac aaaaaaaaaa aaaaaaagag | 4320 |
| aaaaaaaaag gagggtagct ccaccagcca ggaaggtggc agcgctggtg gctgttggat | 4380 |

```
aggctaccta cagtgtctgg caaatactat gcttgaagac tatgctgtga gcaagattcc    4440
tttgtgaagg aacagcttgg acattgtgta tgtcagaggt atacagcaga atagcagtga    4500
ctaacgcttg tgtgggagag caagcatgtc acctcatact tggaataact cactgccata    4560
caaagtctga atcagctttc gtctttgtgc aacacatgta tgtgggagct tttcagctgc    4620
tgaaacctct agtgacagaa aaggaggttt tgttgttcat ttgtaattaa tgttaatcct    4680
atgagtggtg ggagagatag tgaggtagga gatcagcagg acctgttttc tggtcacaac    4740
ccagctaatc agagcatgat ctggtcaaga tgggatgcac taaaaaaaca gcccaaacca    4800
gcagatggcc aggaaagcaa actctcatta ccctcgccac ttattagcat aaagacactc    4860
ccaccggtgc catgacagtt tacaaatgcc atggaaacac accatagcaa cggtcagcaa    4920
gttacctcat atggttctgg aaactcccca cccttttcc agatagttct gaataaccca    4980 cccttaatt tgcatgtaat taaaagtcgg tataagtaca gttagccagc agcccactgg    5040
ctgctactgt gggctcactg cctatgggtt gtcctgctct gcaaggaaca gctaccttgc    5100
tgccactgct gcttcaataa acctgctttc ttccaccaca ggctcgctct tcagttcttt    5160
cctgagcaaa gttaagaacc ctcccgggct aagccccaat tttggagctt gcctgccctg    5220
catcagtaga atgggctaac tacttacggt gcactcaggc taagaggct gatgcttgca    5280 gggcagtatt cacagagcac acggtagttc acgggatgcc tctcaccctt gactcagtgc    5340
ttaagaaagg agggaaaatg gtgaacatga tcaaatcatg gccattgcct attcatcttt    5400
tcagtgttgt atggaggaat aggcaagtag gagattgctt ttcacattaa tgtcaaagag    5460
aaagatagtt acttggaact taaaaaaatt aattgtgata aaatatacat aacataaaat    5520
ttaccatctt aaccattttt aagtatagcc aatctcaaga gctctttcta tcttgtaaaa    5580
ctgaaaccct atacccatta aacaactccc aattctcccc tttccctaac tcctggcaac    5640
cacaattctt tctgtctcta tgaatttgac tgctttggca tgtcatagaa atagactcat    5700
acagcatttg tcttttttgcg actggcatat tttgcttagc ataatgtcct caaggttcac    5760
ccatgtggta gcatgtgtca gaattcctct ccttttgaag gctgaataat attccattgt    5820
gtgtatatac cacgttttgt ttatccattt gcccatcaat gggcatttgg gttgcttttt    5880
ttgcctctca tgaatgatga atatgggcgc acaaatatct cttcaagacc atgctttcaa    5940
ttctcttggg tatacaccca gaagtggaat tgctgaatca tatggtaatt tttttttttt    6000
tttgagacag aatcttgctc tgttgcccag gctggagtgc agtggcacaa tcagagctca    6060
ctgcagcctt ggtcttctgg gctcaagcga tcctcttgct tcagccttcc gagcttctgg    6120
gactaaaggt gtgtgccatc atgcctggct aatgttttaa aaacgttgcc aggcatggtg    6180
gctcgtgctt gtaatcctag cactttggga agctgaggca ggtggatccc ctgaggtcag    6240
gagtttgaga ccagccttgc caacatggtg aaatcccgcc tgtactaaaa atacaaaaat    6300
tagctgggtg tggtggcatg tgcctgtagt tccagctaca ggcaggagaa ttgctggaac    6360
ctgggtggca gaggctgcag tgagccgaga ttgcaccact gcactccagc ctgagtgaca    6420
gagtgagact ctgtctcaaa aaaaaaaaa attttagaga tggtgtctca ctgtgttgcc    6480
caggctggtc ttgaactcct gccctaaagt gatcctcctg cttccgcctc ccaaagtgct    6540
gggattacag gcattagcca ccatgcctgg cctagctaaa ttgtctttaa tgtcgcatgt    6600
ctgcaaaaaa cacatctata aagctagaaa agttgagcat ccaactttt atgatttaac    6660 tctcatgacc tggcaatttt tctagcaagg agcctgggct ggtggtttta ggagaactga    6720
```

-continued

```
gtgaaaaaaa gaaatacatt aactagattg gatgcaaagt gcctgctggt catgggtgtt    6780
ttctgctggc ccctgttcat ctgtgcctgt tagcccaccc atgggtgagt ggggcaaagt    6840
ggccaaactg attcttaaga gaggcataca tgcagaatcc aagttagtca tgatttcgtt    6900
tctagtctga gtgaatgtgt gtccagaata tttataaac tttatcagct cagaggggaa     6960
aacctgtctc catactacgt ggtttataca aagctgtcag gaattcagca tgatgaagaa    7020
atgcacaaaa caagtgtgaa cagataagta aaggatcta ctgaaaatct tcagggtagt     7080
atattgtgtg acaggaccaa gaatttgaag tcaacatctg tatttgtgcc ctctggacaa    7140
aggtattatc cctgatgata taaaaattaa ttttgggctg gtgtggtgg ctcatgcctg     7200 taatcccagc actttgggag gctgaggagg gtgaatcgac tgacgtcagg agttggaggc    7260
cagcctgtat cgactaataa tacaaaaaaa ttagctggaa tggtggcgt gcacctgtaa     7320 tcccagctac tcaggaggct gaggtgggag aattgcttga actcgggagg ccgaggttgc    7380
agtgagtcgc accactgcac tctagcctgg gcgacagagt gagacwccgt ctcaaaataa    7440
acaaaattaa tttcgaggcc aggtgcagtg gctccaggtg cggtggttca tacctgtaat    7500
tccagtgctt taggaggcca gaggattgct tgaacccaac agttcgagat caacctgggc    7560
aacatcagtg agactccatc tgtagaaaac aatcaaacag acaaacaaca acaacaaaaa    7620
aaccagaggt gggaggatca cttgagccca ggagtccgag gctgcagtga gctatggtca    7680
cgccactgcc ctctagcttg ggcaacagtg ccagactctg tccttaacaa caacaacaac    7740
aaaaattaat tctactttaa ctgtcagttt catgatatcc ttctattaag aaaaaccttt    7800
tctatctgat gaactattgg ctaggttttc tttctctctg cttttgacta atgcatttaa    7860
ttactttcat ttgcaaactc tatccttctc atcaactttg tattttagat gtgtctattg    7920
acagcctggc ttccctcagc gatcattatg atgatcaaag tagatgaata ggtaaaattc    7980
aatgcaaata ttccagggca tctaaatcca taccccaaat gggaaaaggg gagaattgga    8040
agccagcaat ttgaacacat tactatggat gtatttttct catgcggggg aaaaagtgat    8100
ttggagagag agaattatga atgcatgtga agaataaagc caaatttcct gggaggaggg    8160
gaagaccagg agaaacaaaa ccaaatcctg gctgcggcct ctaaggcatg gggacctgga    8220
gttatgctct ccaggcagac acagctcatt ctggagaaag gctgcaaaaa tattctcctt    8280
cacattgatt tgaaaacaat tattaaattc ttgttttctt atttatctaa gtgtaacttt    8340
ttaaaactta ctgagagaag acgggcacgg tggctcactg ctgtaatcca gtactttggg    8400
aagtcaaggc aggtggatca cctatggtca ggagttcgag accagcctgg ccaatatggc    8460
aaaaccccgt ctctactaaa aatacaaaaa ttatcaggtg tggtggtgtg tgcctgtaat    8520
cccagctact cgggaggctc agacaggaga atcacttgaa cctgggaggc agaggttgca    8580
atgagctgag attgcaccac tgcactccag cctgggcgac agagcaggac tccatctcaa    8640
aataaaaatt aattgattaa ttaattaaaa atttactgag agctggtggt tcctttaagg    8700
gtggagccgc catcaagtcc ccagaggatg ccctgaattt gggggcatca ccttcagctg    8760
ctgtggactc tgagccttgg cagctccagc tccaggcctg ggagaaagat gatttcctgg    8820
cagcgtgcag tgattgtgag catttgacta ccttactgca ttttgcccct atcaktgctc    8880
tccaaacatg agtggaaaac aaaaaatttt gctgagacaa gcgataatac gagttaggga    8940
aagttggaga atttttatagt tgctgatatc agcaaatcgt gagtttcaag cactaactta    9000
cagaaggaag tccaaaatta aagggggatat agaaatgtgt aaaagatgag gtgtggtgaa    9060
gatggagaaa atgaagagct cttttaaattt ctgaattatg aagaatcacc aacaaattat    9120
```

```
tttgtggttc caaatacagg gagaagttca cagatccaca gaactgatga cagggtgcgg    9180
ccagccacaa acctttcagc acaagaggga gaaggctgcc gctccacttt gcctgggcag    9240
tctttgtaag gcagtagata agtcagcctc gaagttagca atcacagccc tcggctcggt    9300
ttcctgcaag ggcatcgtta atgcatcaca attaatttct tctgtccatt aaatgtcagc    9360
tctcaagtaa attgatgtaa aatttttgta tagaaaacta tttcatatta tttgcacttg    9420
atgtttaatt acatttttaaa tgttttgttt gtttcatttt gttttgtttt tgagacagag    9480
tcttgctctg ttgcccacgc tggaatgcag tggtgtgatc ttgactcact gcaacctctg    9540
cctcctgggt ttaagcgatt ctcctgcctc agcttcctga gtagctggga ttacaggcgt    9600
gcaccaccat gcctggctaa tctttgtatt tttagtagag atggggtttc accatgttgg    9660
ccaggctggt cccgaactcc tgacctcaag ctatacacyt gcctcagcct cccaaagtgc    9720
tggaattaca gacataagcc actgtgccca gccaaatgtt ttaaataatt gtcacatata    9780
tatacaaaat aatttatgtt ataggtaggg atcttgttat attttaacct tcaaagtata    9840
ttcctaagct ttttatttat ttttttatttt ttatttattg agacagtctt gctctgtcgc    9900
ccaggctgga gtgcagtggc gcaatctcga ctcactgcaa actctacctc ctgggttcaa    9960
gcgattctcc tgcctcagcc tcctgagtag ctgggattac aggtgcgcac caccatgccc   10020
agctaatttt tgtatttag tagagacggg gtttcaccat attggccaga gctggtctca   10080
aaactcctga cctcaggtga tccatccacc tcagcctctc aaagtgctgg gattataggt   10140
gtgagccact gcgcctggcc tattcctagc cttttatata tagaccttt tcttttttcac   10200
atttttaaagg aacttttatg tttaatcatg gaatatttca aacatacaga aaaatcacag   10260
aaaataaata acaaccactc atttatcttc tccccaaccc catgtaataa atattaaaat   10320
attgtgttaa atgctaaatt taacacatgc taaaggttcc tggctggatg tggtggctca   10380
cgcctgtaat cccagtactt tgggaggagg aggtgggagg attgcttgag tccaggagct   10440
cgagaccagc atgggcaaca tagtgcgatc tcgtctctac aaaaaacaaa aaaattagct   10500
gggcatggtg gtgtgcatca gtaatcccag tgactgggag gctgaggtgg gagaattgct   10560
tgagtctggg aatttgaggc tgcagtgagc cctgatcatg ccactgcatt ccagcatggg   10620
cgacatagca aaacttgtca aaaaaaaaaa aagtttcctc tctgccccac catagacaac   10680
cactcttctg atttctatct tcgtagatga attttgccca ttctcttgta tatgaaagga   10740
accagacatt aggcattctg gtgtctggtt tctttcactt aagataaaat tgagttaacc   10800
tgtattgttg tacagaactg cagtttgttc tttgttattt attgtaaaga cagggtctgg   10860
ctatgttgcc taggctggtc tcgaactgtt ggcctcaagc aatccacctg ccaagctctg   10920
ggaccacagg catgagccat ggcatctgat ckgtagtttg atcttatttc ttgctgagta   10980
gtagcccatg gcatgacttt attattttgg gtgtccattc tcctctggag gggctctgct   11040
ttttgaaacc acaccctggc ctagctcccc ttctccctgc ctctctgcag gctcacatcc   11100
acatgccaag acctctgcag ccattctgct tcctgtcctt ccactcctgt gggacctcag   11160
agagctacgg ggctccctgg gtaccaactg gctcctgagg cctggggag gtggtcttc    11220
tgggagaagg aagccaggtc cctgcaggtt gtggagggg acagaatgag ggttttttccc   11280
caggatgttg ttggcccctg cccccacttc tgttccataa ttaaccacgc cctcctacc    11340
cactgtgccc ctcttcctgc tgtgtggagg ccctgaatca ttattttaac tacccccctgg   11400
gagggtgagc accttctgtg ctctgtcccc aaccttccac ttcccctcaa cgcgctgctc   11460
```

-continued

```
agggatgacc ttcggcactg tgcttcttct gagtggtaag tggggccagg gtgctgggga    11520
gaagcttgga ggagttctga ggggactcca tctgggaggg caggctgggg gctggtggtc    11580
ggctccaacc actcttatga ggagctgagg cagggagtg cttcatgtgc gagtggcccg     11640
gagtcagtag agtgtgacct gaatgaagag gggctcaggg gctgtgctca ggtggcgact    11700
aagctacctc tccagctggc tatgttgtcc caggcttccc tgctcccact catggagtcc    11760
ctggtgtggg tgacagaggt ctccccagcc tcccccggga gtggaaggcc acagaagcca    11820
ccagggaggg ggaaaggttg gacatcacct ccctgggcct nnnnnttccc ccaagtcctg    11880
actgcacgta gggaagaggc cccctgctga aaactgcatc agagtcacat tcacgtgcca    11940
tcaaaaatca ggcttggctg ggtgcggtgg ctcatgctta taatcccagc actttgggag    12000
gccgagatgg gcgtatcccc tgaggtcagg agtttgtgac cagcctggcc aacatggtga    12060
aaccccatct ttaccaaaaa tataaaaatt agccgggcat ggtggcgtgc acttgtaatc    12120
ccagctactt gggaagctga ggcaagaaa tcgcttgaac ccaggagacg gaagttgcag     12180
tgagctgaga tcgtgccgtt gcactccagc ctcagcaaca gagcgagact ccatctcaaa    12240
aaaaaaaaaa aaaaaagaa aaaaagaaa agaggctgg gaggtcctag ggattggggc       12300
ttctttaact cccagcctcc ccgcccacca aatattcctc agtcctggct tcttatcatg    12360
gattcaacct ggatgtggag gagcctacga tcttccagga ggatgcaggc ggctttgggc    12420
agagcgtggt gcagttcggt ggatctcggt aggccccact caccctcctt ccccaacctc    12480
cactacatca agtcctgtgg atgggtacac gtgggttacc cgagggaggt gtcctggagg    12540
aaggccagca ggggtgagaa gtcttccctt ggctccttgg aggccctgac atcagcacct    12600
attattctca atcccaggaa aggccacaaa actctagaca agaccctacc ttacctcggg    12660
agggaagcct tgaacctgcc tcccaggcag ggcccacttc ttggggccag tatggtcaca    12720
cagggcccac actcattaac tttggagttt aatgttctgc ccttgacctc ttgaaattcc    12780
tgattatttt tatttttatt tttactccag ctctgttacc caggctggag tgcagtggtg    12840
caatcacagc ttactgcagc ctcaaactct cgggcacaag tgatcctctc acctcagcct    12900
cctgaatagc tgggaccaca ggtgcatgcc atcatgcctg ttttttgttt tgttttgttt    12960
tacttttttac agagatggag tcttgctatg ttgtccagac tggctgaact cctgggctca    13020
agcaatcctc ctgccttggc ctcccaaagt gctgggatta caggtgtgag ccaccctgtc    13080
ttgccaattc ttaaaaattt tatctgtgca tttgtgtttt gcaagtaaag aatgatggca    13140
gggctgggca ccatggctca cgcctataat cccaacsctt tgggaggctg aggcgggcag    13200
atcatctgag gccaggagtt tgagaccagt ttggccaaca cagcaaaacc ccatctctac    13260
taaaaatgca aaaaaatta gccgggcatg gtggcaggca tctgtaatcc cagctacttg    13320
ggaggctgag gcaggagaat cgcttgaacc tgggaggtgg aggttgcagt gagccgagat    13380
cgtgccactt tactccagcc taggtgacag agtgagactc cgtcaaaaaa aaaagtcat    13440
gggagaaggg agatgtactg ggggtttgga gccttagctc agcagcagcc ccacctccca    13500
ccgcctcctg aagggtggtg aaggggtatc agctgctggc tccccacccc atgtgggagc    13560
aatgaccgct gctaccttcc gcccctggca tgagctgggt aaagtcagtt aggggcgctc    13620
actctgggag taccccgagg gagtgggaca ctacatagca aataaaaaac gtcaggacag    13680
gttgaggaaa gagagcagaa gaaaggtaag agccccccaa ccccaagaga ccccacagtt    13740
ttatttcaaa ttgggaccca caaattatga acctgccccc acttccagga gctcacattc    13800
tcctgtccca gagagttcaa gtcacaatgt gacacaggtg tcaccaaggt ctgggggcg     13860
```

-continued

```
caggcaggga gagagcagac ccaggagggt tccatggagg aagtggtgct ggcagtgagc    13920
cccagtggac aggaaggctc agttggtcac gaggagctat aagaggtcac cgagctccaa    13980
ccgcgcaccc ctctcccttc ctcatgtgac tggcagtctg gggggatgga agcaagcacc    14040
aggcaccagg cttttgtttt tctttatttg gaaatgtggt caactgaggt gcacaaatct    14100
gaaagaccca atctgataaa ggatacacat gtgcgtgcct gggtgagccc cacctaggtc    14160
agctgctcca gtgtcaaatc ccacaggcac agggctgccg tggaccccct ctcatcaccc    14220
aacatcccca gagaacccct ggtcagactt ctgtcaccat cagttttttg gccacatttt    14280 taaaaaaga atacattggc tgagtgcagt ggcttatgcc tataatccta gaactttggg    14340
aggctgaggc gggtggatca cctaaggtca agagttcaag accagcctga ccaatatggt    14400
gaaaccctgt ctctactaaa aaatacaaaa attagcctgg cgtgatggca ggtgcctgta    14460
atcccagcta gctgggtgac tgaaatagga gatttgcttg aacctgggag gtggaggttg    14520
cagtgagctg agatcacgcc attgcactcc aacctgggtg acagagtgaa actctgtctc    14580
aaaaaacata tggttgatgg ggttacacta aagttttgct catcgtttgt atcagcaggt    14640
tccaaactgc tacctctcta gccaatgctc agattttctt cacaaagcct taggcatccc    14700
ctgaatcatg atgcacaggg attgtagctt tctgtaaagg agcggcacct agaaggaacc    14760
ctcacatggc catttaatga agccttgctt ggcgcattaa aatacaccag tatctgtctg    14820
cttttctcac agacaggaga ttgtgggtag tgagaaaaca tttccaaaat taaaaaactt    14880
tcccactcag ggagttttgc aaataaaccc ttgactctac ataactatag atatagttat    14940
ggatcctagt acactgcttt acattggcca attgaaattg cttatacaat atttaaattg    15000
gtccaatgaa ttacagaatc aactatttgt tttgaaagca catgtcttca ggaaattgtt    15060
ccaattaact tgagatgatc ttatttcttg ggtggttcaa ataatggca actcagaaac     15120 gcaatgtgct tacccatgat tgggaaatgc cattttggtc tttaaatagg tctttttttt    15180
tttttttttt tttttttttt ggtgaatgtt aaaagaaat ttctaaacat aaatacacac     15240
atacgtactt atgcacactc aaaaccaaat aaacccagc atggcccctg gcatctgtg      15300 agttacactt gggccctgat ttctgaatat tctgccaagt ggcaaatgcc aggaatttcc    15360
cccacagagt ctcgcttccc catggaggga cacttcctca cccccaagtg cccgctgctc    15420
ccacccctcc tgtggctgca gtgacatggc catggttgtg tctccagact cgtggtggga    15480
gcaccctggg agtggtggc ggccaaccag acgggacggc tgtatgactg cgcagctgcc      15540
accggcatgt gccagcccat cccgctgcac agtgagtgac cacctgggaa ttgggcccct    15600
caaccctcct ggacccaact gtgccccgc ttagcttcca gtccagacct tccccgcaaa     15660
tgagtgtgtg ctgtgagtga ccccgcgt gtctgccctt gcagtccgcc ctgaggccgt       15720
gaacatgtcc ttgggcctga ccctggcagc ctccaccaac ggctcccggc tcctggtgag    15780
tgagtgtctt gggccacggg ggggtgggt ggggcggggg gtgttgttgg ggaggaggct      15840
ggggctggga gtgaaggagg aggggctgct agggactcct ggctcacagg cttctgcctc    15900
caggcctgtg gcccgaccct gcacagagtc tgtggggaga actcatactc aaagggttcc    15960
tgcctcctgc tgggctcgcg ctgggagatc atccagacag tccccgacgc cacgccaggt    16020
aggtccctgg caggccatgg ttccctgtgg agcacatgct ggcactgagg gtgagcaggc    16080
gtgaggcctg tgtctgggcc cctgtgccct cctggaggg ccgagtgtgg ctaggagaga     16140
agccaggaga agagggtggc tcaggcagga gccctgctgc tccagggtag aagttctttg    16200
```

```
cagggttttt ctttatattt ttttcttttt aagacaggt ccctgccagg cacagtggct    16260
caggcctgta attccagcat tttaggaggc tgaggtgggc gggatcacct gaggtcagga    16320
gttcgagacc agcctggcca atgtggtgaa acccctctac taaaaataca aaacaaaaca    16380
aaacaaaata gcaggatgtg gtggtgtgcg cctgtaatcc cagccactcg ggtaggcaga    16440
gacagaagaa tcgcttgaac ccaggaggcg gaggttgcag tgagctgaga ttgtgccatt    16500
gcactccagc ctgggtgaca agagcaaaac tccatctcaa aaaaaaaaa aaacaaaaa     16560 acagagtttc tgtcaggctg catgcaccac cacaccctgc taattttttt gagacagagt    16620
cttgctctgt cgcccaggct ggagtgcagt ggtgcaatca tagctcactg cagcctcgaa    16680
ctcctgggct caagtgatcc tcctccctta gcctactgag tagttgggac tgcaggtaca    16740
tgcatcacac ctggctaatt aaaaaaaatg tttttgtaga atgggggtc ttgctatgtt     16800 acccagcctg gtcttgaact cctgggctca gtaatcctc tgccacagcc tctcaaagtg     16860
ttgggatgac aggcatgagt ccttgtgcct ggcctgaggg atgaaagttc tgatggaggc    16920
agagaggagc cccactgtgc gggctgtaga gggcacagca tcttccagtt gccaacaggt    16980
gcatggccac ttcttgagtt tcagaggaag gaccttagtt tggtaaagaa cgtggtgagg    17040
aagataaatc catgagggag gtgtttcttc tggatggttc actgctgagc ttccaggatt    17100
ccccaaacta actttcctct cgaagaggag caaatgacag gctgcggaa aatgcgatgt      17160 gcaattttgt cagtgcccat gtcttccaca gagaacaggg cctggggaca ccaccatgac    17220
atctctctga gggttggtct gcatcatggt ggttcccaag tttgttttcc atgggcacca    17280
ggcttcattc ccttgaagct tcattccctc aaagccattc agtttcctca ttggtaaaat    17340
agagctcaat aatcagggg ttatgaaggt gaaagggatt gaggtgcata aagcacttgg      17400
aaccctgcct ggcacatagt atgtgatagc ccctctgacc catcttccag ctggggactg    17460
catgctggga ctgggaggaa gatacaggca aactgtctca tctgccgtgt gagagggaat    17520 gccagggcc gctcagggtg ctgaccgagg gtggggcttc agaccagaga ggccatgatg      17580
acaggcatgc tgggccttta gacaaaggtg gagcagcagc agaaacatta ccagagcaaa    17640
tggtgagggt ggagtctatg gagggggacca agggaagggg gaagggacat ccagggttct   17700
tggggggacc gtgcccagcc tgagatgtct gtgaagctag gttagggagg tggcacttaa    17760
aaacaagggg taaatgtctt ctcacagcca tccgtggaac tcatgaggtg ggatgcctga    17820
tgcaaatggg actggagcac aaaactggtg caggcaaggg gggtgtgggt ccaagtagaa    17880
gggaccaggg tccactgagg atcacctgtg tgccaagcag tgctgaatac ctggtatgaa    17940
tcaccttatt gcatcctcac aacatcctgg gtggtgggca ggcccattct cattttacag    18000
atatgaaaac caaggttcag atagatgagt tccatcgata gcaagaggca gagcccgag     18060 cttgagccat ccttgcctga ttggtggggt ccttttttcaa aaggataagt ccaggcttct    18120
gctagtggga gaccagggga tacaataaaa agaccaagaa acagaagaga cattgtgaga    18180
ggatttgcca cagacctggc ctgagagagg atgagagggt ggtttcttga cgcagctgaa    18240
aaaacaggca ccactgcaag atgttggctg cccagatgtg ggcaaaaaac ggggagctcc    18300 tgggggatc tgcagcctgc cccatggatg tcaagatttg ctggtgattg aagaagcagg      18360
aaggaagtga ccttctgttt ctccccagca cccttgaagc accagtggtt gagcaagtgg    18420
ggtaggggag aggaaagagg aaaaggcatt ttttttttct gcagtggtgg gcagggggca    18480
gaaaccacag ccctgtggtg tgggcctcac accttagtgc tctggtggcc tgatctccca    18540
gtgccctgcg ggcagcacag gatgtggctg ctggtggagg taccaactgg gccctgaaca    18600
```

-continued

```
caggccacac acccccccatg agcctgggga cagcatgaaa agtcttattt gttcatgtgc   18660
atatgatgtg ccctcacgat tgcagagtga actccacaaa ctctgaggtc acttgggaat   18720
gttctttttt tttgagacgg agtctcactc tgtcgcccag gctggagtgc agtggcacaa   18780
tcttggctca ctgcagcctc cacctcccag gttcaagtga ttctcctgcc tcagcccccc   18840
aaatagctag gattacaggc accgccacca tgccgggcta attttttgt attttagta    18900
gagatggggt ttcaccatgt tggccaggct ggttttgaac tcctgacctc aagtaatccg   18960
cccacctcag cgtcccaaag tgctaggatt acaggcgtga ccaccactc ccaactggga   19020
atattcttgg gcaccgcacc catgggagca tgaagggtgg atgcaatgca atcataacag   19080
aggcccaagg tcagcactgg ggtgcttgcc tgtcatccca gtgctttggg aggccgaggt   19140
gagtggatcg ttagagccca ggaggttgag accagcctgg gcaacatggc gaaactccgt   19200
ctctacaaaa agatacaaaa attagccagg caaggtggtg cacacctgta gtcccagcta   19260
ctcaggagac tgaggtggga gaattgcctg agcctgggga ggtcgaggct gcactgacct   19320
gtgatcacac caccacactc cagcctgggt gacagtgaga ctctgcctca aaaaaacaaa   19380
aaatgaaaaa accagaggcc tcagccaatg cctggggggc tcagagtgca gctggccctt   19440
cagacgctga accagtcatc ggtaaaggtt tcctccaggg gcaggaggtg tcccagtggg   19500
caacagttcc cctctgccta gcgtgattcc tgggaaggga ctcagctcag agccaactcc   19560
acgtagctgg aaataaggac ctctgaccga ctgggggtag ggtggggtct ggggtggatc   19620
cctgccccac ccccacagca tccctacagg catatcctac aggcctcgaa ggtgcctggc   19680
acgtggtgag aatggtgcca gcggctgacc ctggcagagg gccaggactt gtctccagca   19740
cccatgtgcg tgttgcttta tccttgcagt gatcccacgt ggtagccact gatattacct   19800
tcattttaca gatagggaca ctgaagtcca gagaagttaa gtaatgtgcc tgaattcacc   19860
aattagcacg tggctgagct gggggtttagc ccaggcacac tggctccaga acacgcgccc  19920
tgaaccactt tgctaaacat tcgcccttga tgcttgtggc accctagca tctgtgttta    19980
atgaatattt gttgattaaa tggatgagga gcccacctgg gtcctgtgtt gtcatccctc   20040
tcttccagg ccatgtggga ggaagggagc aggggctgg ggtggcagac tggggcctcc     20100
tccaaggagg ggtcggaaac taggtgggga tgccaagaac agccccgggg ctctgttgag   20160
caggagctgc aggaggggt tgggcccccg cagtgcatct ccgattcctc cccattcccc    20220
cacagagtgt ccacatcaag agatggacat cgtcttcctg attgacggct ctggaagcat   20280
tgaccaaaat gactttaacc agatgaaggg ctttgtccaa gctgtcatgg gccagtttga   20340
gggcactgac accctggtga agactggca cctggggctg gggtttgggg gacggggag    20400
gctggcctcg gggaggcatc ccgggagggg tgggggcagg ccagtgagcc gtgtgtgatg   20460
gggctggggt ggagaatgaa gctatggtcc cagcacaggc ccaacttgag ccctgaccta   20520
ggaggccctc ttggcatttta ataatgtatc caaaagctac aggaaataca atgtttctgc   20580
tgtttaaaaa cattgaaagt gtttaaaaaa taatttgct atggaatttg actgacatat     20640
tttctatgta actaatgatt tcttttatt atttttatttt cccataacta gtgcctatgt     20700
atgtgcaaaa aaaccccact gttttgtttt ttaaacaggg tcttgttctg tcatccaggc   20760
tgcagtgtgg gggtgcaatc atagctcact gcagacttga tctcccaggc tcaagtgatc   20820
ctctttcctc agcctcctga gtagatggga ctacaggtgc atgccaccat gcctggctaa   20880
tttttaaaaa tttttattgt agagatgggg tcttgttata ttgcccaacc tggtctccaa   20940
```

```
ctcctggctc aaacaaccct cccaccttgg cctctcaaag tgctgggatt acaggcatga    21000
gtcactacgc ccagccacaa attcttgaga agggaggaaa tacacaaatt gatttaatgt    21060
gtgataaaat ttttaaaaag ctaagggtag caaatattgt ggttggcaaa gttattttta    21120
ataaactgtg aaggaaatat catttggttt agattttcca gtttatattt tgtattttttg   21180 ggccaatgaa ttttcttctc tgggtttcag tatattattt gtagggcttc aaaacacatg    21240
ggaaatggtt tgtaaatcca aaataattcc aaaataaagt ttattaaaac tgaaaacaat    21300
atggcttggt gtggtggctc acacctgtaa tcccagcact ttgggaggct ngaggtggga    21360
gtattgcttg aggccaagag ttcgagacca gcctgggcaa catagtgaga ccttgtctct    21420
accaaaaaca aaacaaaaca aaaacaaag ccaggcatgt gacgtgtgcc tgtagttcca     21480
gctacttgga ggctgaggca ggaggatcac ttgaggccag gagtttgaga gaccctgtct    21540
ctacaaaaaa ttaaaataaa aacaatagta acaggcactg agccctgggc cctccccact    21600
ggcctttgca gtttgcactg atgcagtact caaacctcct gaagatccac ttcaccttca    21660
cccaattccg gaccagcccg agccagcaga gcctggtgga tcccatcgtc caactgaaag    21720
gcctgacgtt cacggccacg ggcatcctga cagtggtgta aagcaaccc gacccca       21777
```

<210> SEQ ID NO 4
<211> LENGTH: 25
<212> TYPE: DNA
<213> ORGANISM: Homo sapiens

<400> SEQUENCE: 4
cctgaatcat tattttaact acccc                                          25

<210> SEQ ID NO 5
<211> LENGTH: 23
<212> TYPE: DNA
<213> ORGANISM: Homo sapiens

<400> SEQUENCE: 5
ccataattaa ccacgcccct cct                                            23

<210> SEQ ID NO 6
<211> LENGTH: 23
<212> TYPE: DNA
<213> ORGANISM: Homo sapiens

<400> SEQUENCE: 6
acccactgtg cccctcttcc tgc                                            23

<210> SEQ ID NO 7
<211> LENGTH: 24
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 7
gcggtgatcc cgggtgatct gaat                                           24

<210> SEQ ID NO 8
<211> LENGTH: 10
<212> TYPE: DNA
<213> ORGANISM: Unknown
<220> FEATURE:
<221> NAME/KEY: misc_feature

```
<222> LOCATION: ()..()
<223> OTHER INFORMATION: primer

<400> SEQUENCE: 8
attcagatca                                                           10

<210> SEQ ID NO 9
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 9
ctgggagaag gaagccaggt c                                              21

<210> SEQ ID NO 10
<211> LENGTH: 27
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 10
caggttgtgg aggggacag aatgagg                                         27

<210> SEQ ID NO 11
<211> LENGTH: 33
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 11
ggttgtggag ggggacagaa tgagggtttt tcc                                 33
```